US012605101B2

(12) United States Patent
Qu et al.

(10) Patent No.: US 12,605,101 B2
(45) Date of Patent: Apr. 21, 2026

(54) SYSTEMS AND METHODS FOR IMPROVING VISIBILITY OF FEATURES OF PHYSIOLOGIC SIGNAL SEGMENTS

(71) Applicant: Pacesetter, Inc., Sylmar, CA (US)

(72) Inventors: Fujian Qu, San Jose, CA (US); Praveen Gopalakrishna, Sunnyvale, CA (US); Tejpal Singh, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 350 days.

(21) Appl. No.: 18/461,235

(22) Filed: Sep. 5, 2023

(65) Prior Publication Data

US 2024/0156387 A1 May 16, 2024

Related U.S. Application Data

(60) Provisional application No. 63/425,876, filed on Nov. 16, 2022.

(51) Int. Cl.
*A61B 5/339* (2021.01)
*A61B 5/00* (2006.01)
*A61B 5/349* (2021.01)

(52) U.S. Cl.
CPC .............. *A61B 5/339* (2021.01); *A61B 5/349* (2021.01); *A61B 5/7264* (2013.01); *A61B 5/743* (2013.01)

(58) Field of Classification Search
None
See application file for complete search history.

(56) References Cited

U.S. PATENT DOCUMENTS 6,266,566 B1 * 7/2001 Nichols .............. A61N 1/37247
607/30
7,819,813 B2 10/2010 Nagai et al.
(Continued)

FOREIGN PATENT DOCUMENTS

EP 3620107 A1 * 3/2020 ........... A61B 5/6831

OTHER PUBLICATIONS

Non-final Office Action dated Oct. 22, 2025, U.S. Appl. No. 18/490,637, filed Oct. 19, 2023.
(Continued)

*Primary Examiner* — Kennedy Schaetzle
(74) *Attorney, Agent, or Firm* — Pearl Cohen Zedek Latzer Baratz LLP

(57) ABSTRACT

Systems and methods described herein improve visibility of features (e.g., P-waves) of a physiologic signal segment (e.g., an EGM or ECG signal segment) to be displayed within a display band having a specified height between an upper and a lower boundary of the display band. The physiologic signal segment is divided into sub-segments, for each of which a sub-segment minimum peak amplitude and maximum peak amplitude are determined. Based thereon, a new minimum peak amplitude and a new maximum peak amplitude are determined and used to determine a new display range. A portion of the physiologic signal segment that is within the new display range is caused to be display, within the display band having the specified height, such that the upper boundary of the display band corresponds to the new maximum peak amplitude, and the lower boundary of the display band corresponds to the new minimum peak amplitude.

25 Claims, 9 Drawing Sheets

(56) References Cited

U.S. PATENT DOCUMENTS

| | | | |
|---|---|---|---|
| 10,251,573 B2 | 4/2019 | Ousdigian et al. | |
| 2006/0100536 A1* | 5/2006 | Nagai .................... | A61B 5/339 |
| | | | 600/519 |
| 2015/0342485 A1* | 12/2015 | Hertel .................... | A61B 5/339 |
| | | | 600/300 |
| 2022/0133168 A1 | 5/2022 | Reisfeld et al. | |

OTHER PUBLICATIONS

Response to Office Action dated Dec. 17, 2025, U.S. Appl. No. 18/490,637, filed Oct. 19, 2023.

* cited by examiner

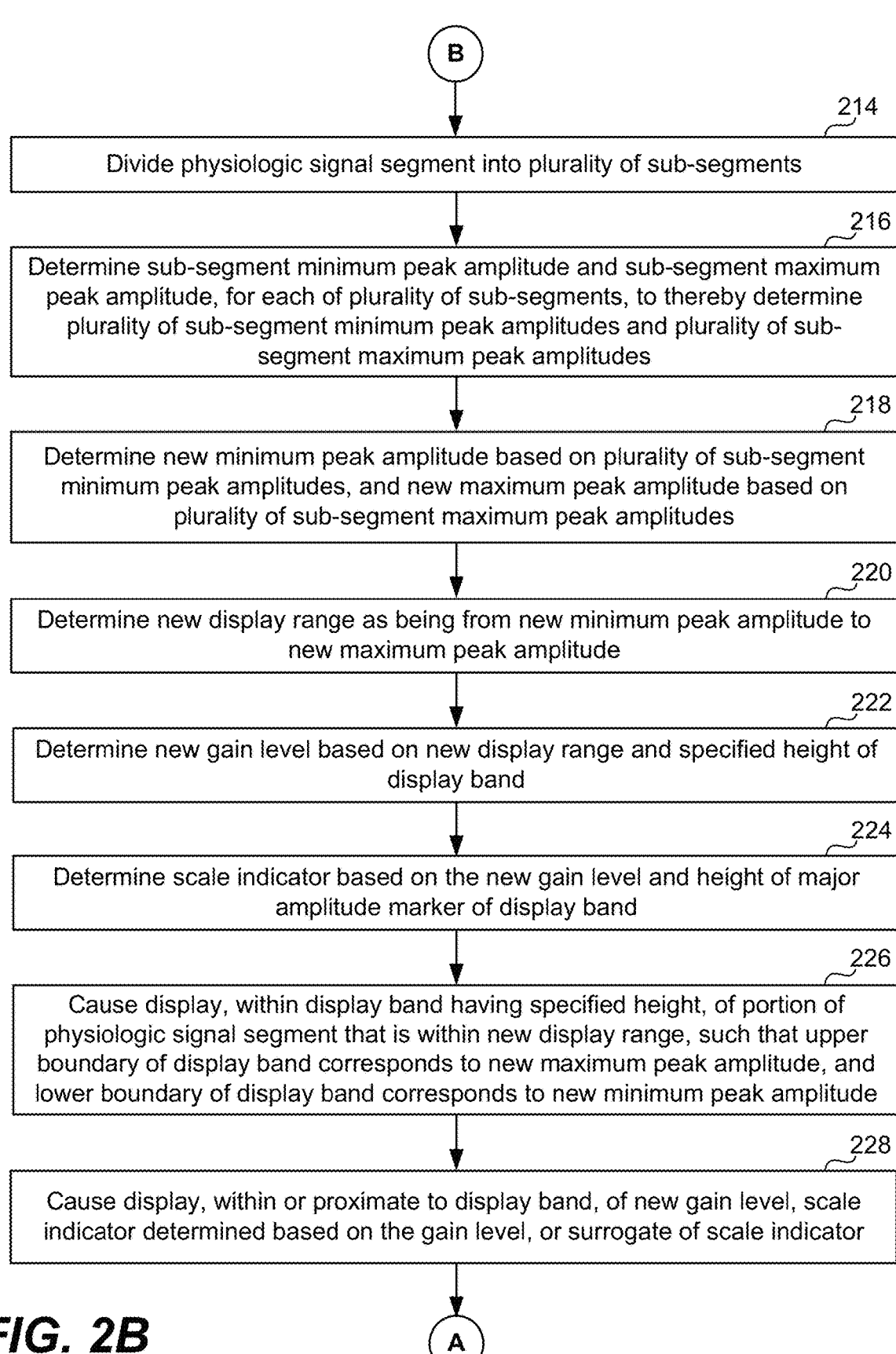

Divide physiologic signal segment into plurality of sub-segments

216

Determine sub-segment minimum peak amplitude and sub-segment maximum peak amplitude, for each of plurality of sub-segments, to thereby determine plurality of sub-segment minimum peak amplitudes and plurality of sub-segment maximum peak amplitudes

218

Determine new minimum peak amplitude based on plurality of sub-segment minimum peak amplitudes, and new maximum peak amplitude based on plurality of sub-segment maximum peak amplitudes

220

Determine new display range as being from new minimum peak amplitude to new maximum peak amplitude

222

Determine new gain level based on new display range and specified height of display band

224

Determine scale indicator based on the new gain level and height of major amplitude marker of display band

226

Cause display, within display band having specified height, of portion of physiologic signal segment that is within new display range, such that upper boundary of display band corresponds to new maximum peak amplitude, and lower boundary of display band corresponds to new minimum peak amplitude

228

Cause display, within or proximate to display band, of new gain level, scale indicator determined based on the gain level, or surrogate of scale indicator (A)

| Sub-Segment No. | Sub-Segment max peak amp (mV) | Sub-Segment min peak amp (mV) | | | | | | |
|---|---|---|---|---|---|---|---|---|
| 1 | 0.04094 | -0.05039 | | Vmax 25% quartile = 0.0441 mV | | | | |
| 2 | 0.04094 | -0.05354 | | Vmax 75% quartile = 0.0472 mV | | | | |
| 3 | 0.04724 | -0.05039 | | Vmax IQR = 0.0032 mV | | | | |
| 4 | 0.04094 | -0.05354 | | Vmax outlier threshold = 0.0567 mV | | | | |
| 5 | 0.04409 | -0.05039 | | Vmax outlier index = 32-37 | | | | |
| 6 | 0.04409 | -0.05039 | | New Max option1 = 0.0952 mV | | | | |
| 7 | 0.04409 | -0.05039 | | New Max option2 = 0.0504 mV | | | | |
| 8 | 0.04409 | -0.05039 | | New Max = 0.0952 mV | | | | |
| 9 | 0.04409 | -0.05039 | | | | | | |
| 10 | 0.04409 | -0.05354 | | Vmin 25% quartile = -0.0567 mV | | | | |
| 11 | 0.05039 | -0.05669 | | Vmin 75% quartile = -0.0504 mV | | | | |
| 12 | 0.05039 | -0.05039 | | Vmin IQR = 0.0063 mV | | | | |
| 13 | 0.04409 | -0.05354 | | Vmin outlier threshold = -0.0756 mV | | | | |
| 14 | 0.04094 | -0.05669 | | Vmin outlier index = 32-37 | | | | |
| 15 | 0.04409 | -0.05039 | | New Min option1 = -0.1099 mV | | | | |
| 16 | 0.04409 | -0.05039 | | New Min option2 = -0.0567 mV | | | | |
| 17 | 0.04094 | -0.05669 | | New Min = -0.1099 mV | | | | |
| 18 | 0.04409 | -0.05039 | | | | | | |
| 19 | 0.04094 | -0.05039 | | | | | | |
| 20 | 0.04409 | -0.05354 | | | | | | |
| 21 | 0.04409 | -0.05039 | | | | | | |
| 22 | 0.04409 | -0.05039 | | | | | | |
| 23 | 0.04409 | -0.05354 | | | | | | |
| 24 | 0.04409 | -0.05354 | | | | | | |
| 25 | 0.04409 | -0.05039 | | | | | | |
| 26 | 0.04409 | -0.05039 | | | | | | |
| 27 | 0.04409 | -0.05669 | | | | | | |
| 28 | 0.04494 | -0.05669 | | | | | | |
| 29 | 0.04409 | -0.04724 | | | | | | |
| 30 | 0.04409 | -0.05669 | | | | | | |
| 31 | 0.04724 | -0.05039 | | | | | | |
| 32 | 0.4 | -0.07874 | | | | | | |
| 33 | 0.12283 | -0.4 | | | | | | |
| 34 | 0.08819 | -0.12598 | | | | | | |
| 35 | 0.06614 | -0.10709 | | | | | | |
| 36 | 0.06614 | -0.10709 | | | | | | |
| 37 | 0.07244 | -0.12283 | | | | | | |

*FIG. 5*

SYSTEMS AND METHODS FOR IMPROVING VISIBILITY OF FEATURES OF PHYSIOLOGIC SIGNAL SEGMENTS

PRIORITY CLAIM

The present application claims priority to U.S. Provisional Patent Application No. 63/425,876, filed Nov. 16, 2022, which is incorporated herein by reference.

FIELD

Embodiments of the present technology described herein generally relate to systems and methods for improving visibility of features (aka components) of physiologic signal segments, such as, but not limited to, electrogram (EGM) or electrocardiogram (ECG) signal segments.

BACKGROUND

Various types of medical devices are capable of sensing and storing physiologic signal segments in memory, so that the physiologic signal segments can thereafter be transmitted to a system that is configured to display the physiologic signal segments to one or more persons, such as one or more clinicians. For example, an implantable medical device (IMD) may continuously sense an electrogram (EGM) signal, monitor a patient's cardiac rhythm based on the EGM signal, and store one or more EGM signal segments in memory of the IMD in response to one or more triggering conditions, such as arrhythmia detections, but not limited thereto. The IMD may thereafter transmit the recorded one or more EGM segments to a remote monitoring server system, so that a clinician can view and analyze the EGM signal segments when displayed to the clinician. The quality of displayed EGM signal segments, as well as other types of displayed physiologic signal segments, affect a clinician's ability to adjudicate device detections and make appropriate diagnosis for patient management. This issue is especially evident when a clinician needs to visualize small signal components, such as P-waves, to determine an underlying cardiac rhythm associated with an EGM signal segment.

Conventionally, when an EGM signal segment is displayed to a clinician, all sample points of the EGM signal segment are displayed within a display band having a specified height, so that both the maximum and minimum peaks of the EGM signal segment can be seen by the clinician. Although the minimum and maximum peaks of an EGM signal segment typically correspond to peaks of QRS complexes (indicative of ventricular depolarizations), the minimum and maximum peaks in an EGM signal segment can sometimes correspond to non-physiologic peaks (such as noise artifacts and signal saturation), an isolated premature ventricular contraction (PVC) beat, or the like. When an EGM signal segment is displayed in this manner, it is often difficult and sometimes impossible for a clinician to observe small signal components of the EGM signal segment, such as P-waves, which are indicative of atrial depolarizations, and thus, are important for diagnosing atrial arrhythmias.

SUMMARY

Certain embodiments of the present technology relate to systems and methods for improving visibility of features (e.g., P-waves) of a physiologic signal segment (e.g., an EGM or ECG signal segment) that is to be displayed within a display band having a specified height between an upper boundary and a lower boundary of the display band.

In accordance with certain embodiments, such a method includes obtaining the physiologic signal segment, which is indicative of physiologic activity of a patient for a period of time that includes a plurality of cycles of the physiologic activity, wherein the physiologic signal segment has an original signal segment range that extends from an original minimum peak amplitude of the physiologic signal segment to an original maximum peak amplitude of the physiologic signal segment. The method also includes dividing the physiologic signal segment into a plurality of sub-segments, and determining a sub-segment minimum peak amplitude and a sub-segment maximum peak amplitude, for each of the plurality of sub-segments, to thereby determine a plurality of sub-segment minimum peak amplitudes and a plurality of sub-segment maximum peak amplitudes. The method also includes determining a new minimum peak amplitude based on the plurality of sub-segment minimum peak amplitudes, and a new maximum peak amplitude based on the plurality of sub-segment maximum peak amplitudes, and determining a new display range as being from the new minimum peak amplitude to the new maximum peak amplitude, wherein the new display range is narrower than the original signal segment range. The method further includes causing displaying, within the display band having the specified height, of a portion of the physiologic signal segment that is within the new display range, such that the upper boundary of the display band corresponds to the new maximum peak amplitude, and the lower boundary of the display band corresponds to the new minimum peak amplitude.

Certain embodiments of the present technology also include determining a new gain level based on the new display range and the specified height of the display band, and causing further displaying, within or proximate to the display band, of at least one of the new gain level, a scale indicator determined based on the new gain level, or a surrogate of the scale indicator, to thereby enable someone viewing the display band to discern magnitudes of the features of the portion of the physiologic signal segment being displayed within the display band.

In accordance with certain embodiments, the method also includes determining the scale indicator by determining a quotient of the specified height of the display band divided by the new gain level. In such an embodiment, the causing further displaying comprises causing displaying of the scale indicator or the surrogate of the scale indicator in at least one of the following manners: cause displaying of one or more values along a vertical axis of the display band based on the scale indicator; or cause displaying of the scale indicator next to a vertical line or square wave within or proximate to the display band. In accordance with certain embodiments, the new gain level is determined by determining a quotient of the specified height of the display band divided by the new display range.

In accordance with certain embodiments, the causing displaying, within the display band having the specified height, of portions of the physiologic signal segment that are within the new display range, such that the upper boundary of the display band corresponds to the new maximum peak amplitude, and the lower boundary of the display band corresponds to the new minimum peak amplitude, magnifies features of the physiologic signal segment that are within the new display range, compared to if an entirety of the physiologic signal segment within the original signal segment range were instead caused to be displayed within the display band having the specified height such that the upper boundary of the display band corresponded to the original maximum peak amplitude of the physiologic signal segment, and the lower boundary of the display band corresponded to the original minimum peak amplitude of the physiologic signal segment.

In accordance with certain embodiments, the method further comprises, after the obtaining the physiologic signal segment, and prior to performing any other steps of the method, determining a threshold signal range by determining a quotient of the specified height of the display band divided by an original gain level, and determining whether the original signal segment range exceeds the threshold signal range. The method then includes performing the other steps of the method, in response to the original signal segment range exceeding the threshold signal range.

In accordance with certain embodiments, the determining the new minimum peak amplitude, based on the plurality of sub-segment minimum peak amplitudes, comprises: determining a first outlier threshold based on the plurality of sub-segment minimum peak amplitudes; separating the plurality of sub-segment minimum peak amplitudes into first and second subsets thereof, such that the first subset includes each of the sub-segment minimum peak amplitudes this is less than the first outlier threshold, and the second subset includes each of the sub-segment minimum peak amplitudes that is not less than the first outlier threshold; determining a first candidate for being the new minimum peak amplitude based on the first subset of the plurality of sub-segment minimum peak amplitudes, and a second candidate for being the new minimum peak amplitude based on the second subset of the plurality of sub-segment minimum peak amplitudes; and selecting, as the new minimum peak amplitude, a minimum one of the first and second candidates for being the new minimum peak amplitude.

In accordance with certain embodiments, the determining the new maximum peak amplitude, based on the plurality of sub-segment maximum peak amplitudes, comprises: determining a second outlier threshold based on the plurality of sub-segment maximum peak amplitudes; separating the plurality of sub-segment maximum peak amplitudes into first and second subsets thereof, such that the first subset includes each of the sub-segment maximum peak amplitudes that is greater than the second outlier threshold, and the second subset includes each of the sub-segment maximum peak amplitudes that is not greater than the second outlier threshold; determining a first candidate for being the new maximum peak amplitude based on the first subset of the plurality of sub-segment maximum peak amplitudes, and a second candidate for being the new maximum peak amplitude based on the second subset of the plurality of sub-segment maximum peak amplitudes; and selecting, as the new maximum peak amplitude, a maximum one of the first and second candidates for being the new maximum peak amplitude.

In accordance with certain embodiments, the determining the first outlier threshold based on the plurality of sub-segment minimum peak amplitudes comprises: determining a 25% quartile value and an inter-quartile range (IQR) of the plurality of sub-segment minimum peak amplitudes; and determining the first outlier threshold based on the 25% quartile value and the IQR of the plurality of sub-segment minimum peak amplitudes; and the determining the second outlier threshold based on the plurality of sub-segment maximum peak amplitudes comprises: determining a 75% quartile value and an inter-quartile range (IQR) of the plurality of sub-segment maximum peak amplitudes; and

4 determining the second outlier threshold based on the 75% quartile value and the IQR of the plurality of sub-segment maximum peak amplitudes.

In accordance with alternative embodiments, the determining the first outlier threshold based on the plurality of sub-segment minimum peak amplitudes comprises: determining a mean and a standard deviation (SD) of the plurality of sub-segment minimum peak amplitudes; and determining the first outlier threshold based on the mean and the SD of the plurality of sub-segment minimum peak amplitudes; and the determining the second outlier threshold based on the plurality of sub-segment maximum peak amplitudes comprises: determining a mean and a standard deviation (SD) of the plurality of sub-segment maximum peak amplitudes; and determining the second outlier threshold based on the mean and the SD of the plurality of sub-segment maximum peak amplitudes.

In accordance with certain embodiments, the physiologic signal segment is indicative of one of the following: cardiac electrical activity of the patient for a period of time that includes a plurality of cardiac cycles; cardiac mechanical activity of the patient for a period of time that includes a plurality of cardiac cycles; or respiratory activity of the patient for a period of time that includes a plurality of respiratory cycles.

Certain embodiments of the present technology relate to a system for improving visibility of features of a physiologic signal segment that is to be displayed within a display band having a specified height between an upper boundary and a lower boundary of the display band. Such a system comprises memory configured to store specific executable instructions, and one or more processors configured to execute the specific executable instructions to: obtain the physiologic signal segment, which is indicative of physiologic activity of a patient for a period of time that includes a plurality of cycles of the physiologic activity, wherein the physiologic signal segment has an original signal segment range that extends from an original minimum peak amplitude of the physiologic signal segment to an original maximum peak amplitude of the physiologic signal segment; divide the physiologic signal segment into a plurality of sub-segments; determine a sub-segment minimum peak amplitude and a sub-segment maximum peak amplitude, for each of the plurality of sub-segments, to thereby determine a plurality of sub-segment minimum peak amplitudes and a plurality of sub-segment maximum peak amplitudes; determine a new minimum peak amplitude based on the plurality of sub-segment minimum peak amplitudes, and a new maximum peak amplitude based on the plurality of sub-segment maximum peak amplitudes; determine a new display range as being from the new minimum peak amplitude to the new maximum peak amplitude, wherein the new display range is narrower than the original signal segment range; and cause display, within the display band having the specified height, of a portion of the physiologic signal segment that is within the new display range, such that the upper boundary of the display band corresponds to the new maximum peak amplitude, and the lower boundary of the display band corresponds to the new minimum peak amplitude.

In accordance with certain embodiments, the one or more processors are further configured to: determine a new gain level based on the new display range and the specified height of the display band; and cause further display, within or proximate to the display band, of at least one of the new gain level, a scale indicator determined based on the new gain level, or a surrogate of the scale indicator, to thereby enable someone viewing the display band to discern magnitudes of the features of the portion of the physiologic signal segment that is caused to be displayed within the display band.

In accordance with certain embodiments, the one or more processors are further configured to determine the scale indicator by determining a quotient of the specified height of the display band divided by the new gain level. The one or more processors are further configured cause the further display in at least one of the following manners: cause display of one or more values along a vertical axis of the display band based on the scale indicator; or cause display of the scale indicator next to a vertical line or square wave within or proximate to the display band.

In accordance with certain embodiments, the one or more processors are further configured to determine the new gain level by determining a quotient of the specified height of the display band divided by the new display range.

In accordance with certain embodiments, after the physiologic signal segment is obtained, the one or more processors are configured to: determine a threshold signal range by determining a quotient of the specified height of the display band divided by an original gain level; and determine whether the original signal segment range exceeds the threshold signal range; and cause display, within the display band having the specified height, of the portion of the physiologic signal segment that is within the new display range, in response to the original signal segment range exceeding the threshold signal range, and otherwise cause display within the display band of an entirety of the physiologic signal segment within the original signal segment range.

In accordance with certain embodiments, the one or more processors are further configured to: determine the new minimum peak amplitude, based on the plurality of sub-segment minimum peak amplitudes, by: determining a first outlier threshold based on the plurality of sub-segment minimum peak amplitudes; separating the plurality of sub-segment minimum peak amplitudes into first and second subsets thereof, such that the first subset includes each of the sub-segment minimum peak amplitudes this is less than the first outlier threshold, and the second subset includes each of the sub-segment minimum peak amplitudes that is not less than the first outlier threshold; determining a first candidate for being the new minimum peak amplitude based on the first subset of the plurality of sub-segment minimum peak amplitudes, and a second candidate for being the new minimum peak amplitude based on the second subset of the plurality of sub-segment minimum peak amplitudes; and selecting, as the new minimum peak amplitude, a minimum one of the first and second candidates for being the new minimum peak amplitude In accordance with certain embodiments, the one or more processors are further configured to determine the new maximum peak amplitude, based on the plurality of sub-segment maximum peak amplitudes, by: determining a second outlier threshold based on the plurality of sub-segment maximum peak amplitudes; separating the plurality of sub-segment maximum peak amplitudes into first and second subsets thereof, such that the first subset includes each of the sub-segment maximum peak amplitudes that is greater than the second outlier threshold, and the second subset includes each of the sub-segment maximum peak amplitudes that is not greater than the second outlier threshold; determining a first candidate for being the new maximum peak amplitude based on the first subset of the plurality of sub-segment maximum peak amplitudes, and a second candidate for being the new maximum peak amplitude based on the second subset of the plurality of sub-segment maximum peak amplitudes; and selecting, as the new maximum peak amplitude, a maximum one of the first and second candidates for being the new maximum peak amplitude.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF DRAWINGS

Embodiments of the present technology relating to both structure and method of operation may best be understood by referring to the following description and accompanying drawings, in which similar reference characters denote similar elements throughout the several views:

FIGS. 2A and 2B, which can be collectively referred to as FIG. 2, illustrate a high level flow diagram used to summarize methods according to various embodiments of the present technology.

FIG. 5 includes a table of various values used to describe how the EGM signal segment displayed within the display band shown in FIG. 4 was caused to be displayed.

DETAILED DESCRIPTION

Figure 1:
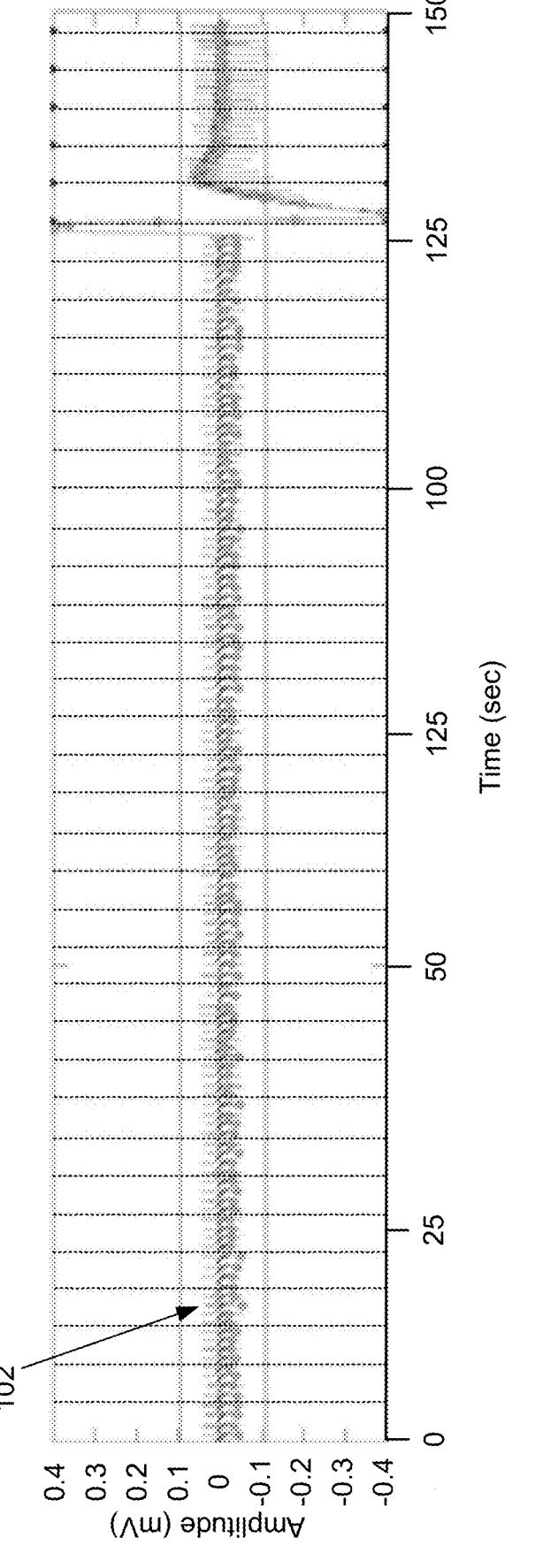
FIG. 1 illustrates an example EGM signal segment that may be sensed by an IMD, stored in memory of the IMD, and thereafter transmitted to an external system that displays the EGM signal segment, or one or more portion(s) thereof, to a clinician that analyzes the EGM signal segment.

Certain embodiments of the present technology are directed to systems and methods for improving visibility of features (aka components) of a physiologic signal segment that is to be displayed within a display band having a specified height. For much of this description, it will be assumed that the physiologic signal segment that is being displayed is a segment of an electrogram (EGM) or electrocardiogram (ECG) signal, which is indicative of cardiac electrical activity of the patient for a period of time that includes a plurality of cardiac cycles. However, as will be described in additional detail below, embodiments of the present technology can also be used with other types of physiologic signals, which are indicative of some other type of physiologic activity of a patient for a period of time that includes a plurality of cycles of the physiologic activity. It is noted that the terms "features of a physiologic signal segment" and "components of a physiologic signal segment" are used interchangeably herein.

The term physiologic signal, as used to herein, refers to an analog or digital electrical signal sensed using two or more electrodes or a sensor (aka transducer), and optionally processed, e.g., using one or more amplifiers and/or one or filters, but not limited thereto. The term physiologic signal segment, as used herein, refers to a temporal segment of a sensed physiologic signal having a non-infinite duration. Such a physiologic signal segment may be stored in a memory of a device in response to a triggering event being detected, such as, but not limited to, an abnormal physiologic event being detected. Examples of abnormal physiologic events that when detected, may trigger the storage of a corresponding physiologic signal segment, include a cardiac arrhythmia, an increase in heart failure burden, and an apnea event, but are not limited thereto. The sensing and/or storage of a physiologic signal segment can alternatively be triggered into response to other types of events, such as a patient being simultaneously supine and inactive, or a patient changing their posture. It is also possible that physiologic signal segments are periodically sensed and stored by a device so that variations in the physiologic signal segments over time can be identified and used to determine changes to a physiologic condition of a patient, e.g., due to therapy and/or medication. These are just a few examples, which are not intended to be all encompassing.

As noted above, conventionally, when an EGM signal segment is displayed to a clinician, all sample points of the EGM signal segment are displayed within a display band having a specified height, so that both the maximum and minimum peaks of the EGM signal segment can be seen by the clinician. Although the minimum and maximum peaks of an EGM signal segment typically correspond to peaks of QRS complexes, the minimum and/or maximum values in an EGM signal segment can sometimes correspond to noise artifacts, signal saturation, a PVC beat, or the like. When an EGM signal segment is displayed in this manner, it is often difficult and sometimes impossible for a clinician to observe small signal components of the EGM signal segment, such as P-waves indicative of atrial depolarizations.

FIG. 1 illustrates an example EGM signal segment that may be sensed by an implantable medical device (IMD), stored in memory of the IMD, and thereafter transmitted to an external system that displays the EGM signal segment, or one or more portion(s) thereof, to a clinician that analyzes the EGM signal segment. More specifically, FIG. 1 illustrates an example EGM signal segment 102 that can be sensed using a pair of electrodes of an IMD, wherein the EGM signal segment 102 has a duration of 150 seconds (sec). As can be appreciated from FIG. 1, for about the first 125 seconds of the duration of the EGM signal segment 102, the minimum peaks of the of the EGM signal segment are greater than −0.1 mV, and the maximum peaks of the EGM signal segment are less than +0.1 mV, wherein such minimum and maximum peaks correspond to QRS complexes, and more generally, to R-waves. However, starting at about 126 seconds there is a cycle of the EGM signal segment that has significantly greater peaks, which were caused by signal drift and saturation. Thus, it can be appreciated from FIG. 1 that an original signal range of the EGM signal segment 102 is 0.80 mV, which extends from −0.4 mV to +0.4 mV. Accordingly, in order for the entire signal range to be viewed within a display band, the QRS complexes within the first 125 seconds of the EGM signal segment 102 would look quite small within the display band, and the P-waves would be difficult to see, if they can be seen at all.

Figure 2A:
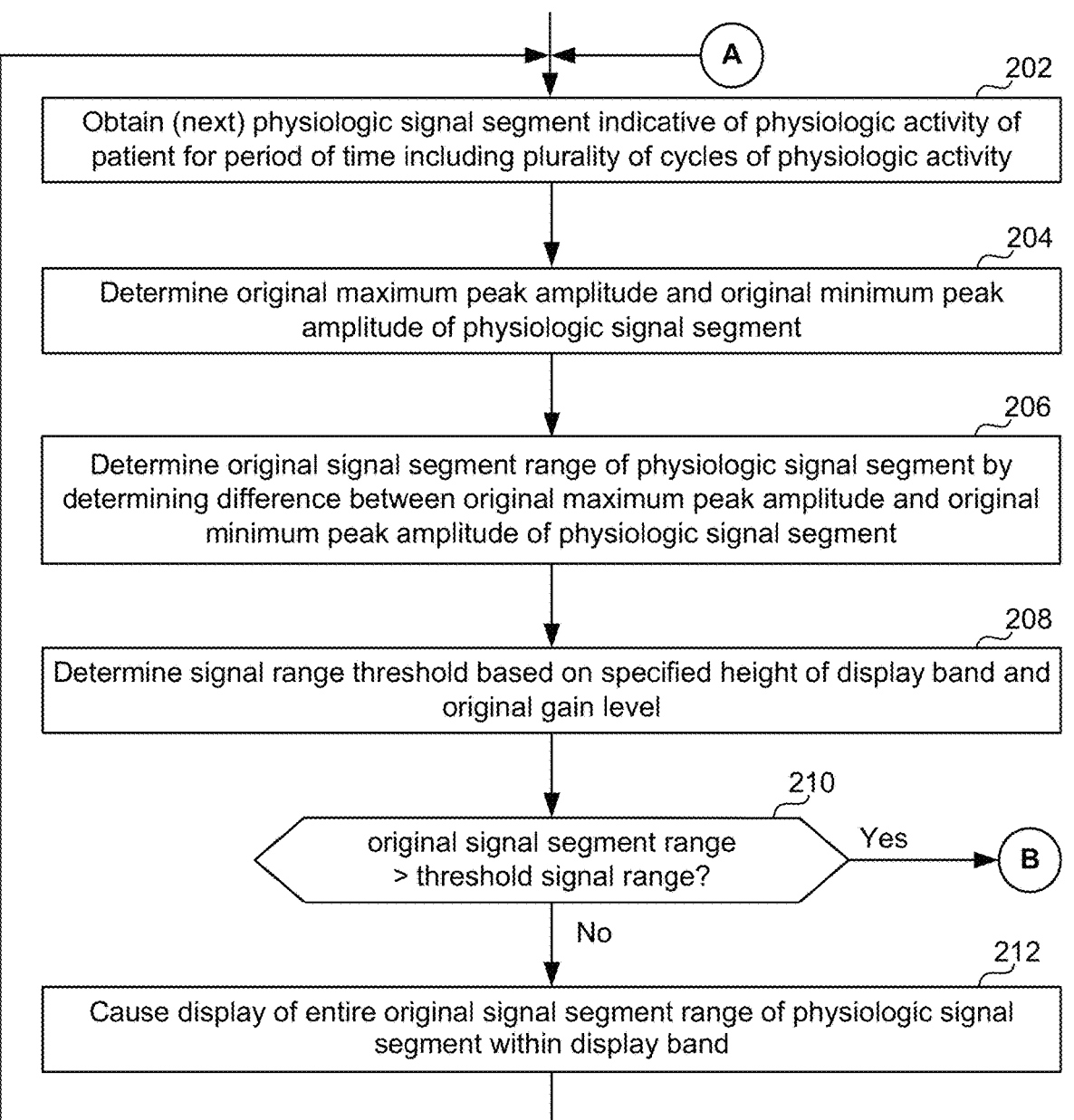

In accordance with certain embodiments of the present technology, which are initially summarized with reference to the high level flow diagram of FIGS. 2A and 2B, in certain situations, where there is/are one or more outlier peaks within an EGM signal segment, a new display range is identified and used to display portions of the EGM signal segment within the new display range. This will result in one or more peaks (and more generally, one or more portion(s)) of the EGM signal segment not being displayed within the display band having the specified height. However, the beneficial tradeoff is that the remaining portions of the EGM signal segment, which includes small signal components, such as P-waves, are more visible to a clinician or other person viewing the EGM signal segment within the display band.

Embodiments of the present technology, which are summarized below with reference to the high level flow diagram of FIG. 2 (which collectively includes FIGS. 2A and 2B), are used for improving visibility of features of a physiologic signal segment that is to be displayed within a display band having a specified height. A display band, as the term is used herein, refers to a region within which an EGM signal segment, or other type of physiologic signal segment, is to be displayed on a display screen (e.g., a display monitor, tablet touch screen, or the like) or on a printout. An example of a specified height of a display band is 20 mm. As will be discussed in further detail below, a display band may include multiple panels that are displayed one on top of the other, in a similar manner that words in a sentence may be included on multiple lines of text that are displayed one on top of the other.

Referring to FIG. 2A, step 202 involves obtaining a physiologic signal segment (e.g., an EGM signal segment), which is indicative of physiologic activity (e.g., cardiac activity) of a patient for a period of time that includes a plurality of cycles of the physiologic activity (e.g., a plurality of cycles of cardiac activity). Step 202 can include sensing the physiologic signal using two or more electrodes or a sensor, as will be discussed in additional detail below. Alternatively, step 202 can be performed by receiving the physiologic signal segment, directly, or indirectly, from memory of a device that includes two or more electrodes or a sensor that were/was used to sense the physiologic signal segment, which after being sensed, is stored in the memory. Step 202 may also be performed by a system that retrieves a physiologic signal segment from a database, memory or other type of date storage. The physiologic signal segment obtained at step 202 can be, e.g., an EGM signal segment obtained from the memory of an IMD that includes, or is coupled to, electrodes that sensed the EGM signal segment and then stored the EGM signal segment in the memory of the IMD. Additional and alternative details of step 202 are described below.

Still referring to FIG. 2A, step 204 involves determining an original maximum peak amplitude and an original minimum peak amplitude of the physiologic signal segment (obtained at step 202), and step 206 involves determining an original signal segment range of the physiologic signal segment by determining a difference between the original maximum peak amplitude and the original minimum peak amplitude of physiologic signal segment. Assume, for example, that at step 204 there is a determination that the original maximum peak amplitude is +0.8 mV and the original minimum peak amplitude is −0.8 mV. Continuing with this example, the original signal segment range determined at step 206 would be 1.6 mV, which is determined by determining the difference between the +0.8 mV original maximum peak amplitude and the −0.8 mV original minimum peak amplitude of the physiologic signal segment (i.e., +0.8 mV−(−0.8 mV)=1.6 mV). In other words, the original signal segment range can be determined using the equation: original signal segment range=original maximum peak amplitude−original minimum peak amplitude=+0.8 mV−(−0.8 mV)=1.6 mV.

Still referring to FIG. 2A, step 208 involves determining a signal range threshold based on the specified height of the display band and an original gain level. The original gain level can be predetermined for a system or device, or can be a desired gain level selected by a user (e.g., clinician) using a user interface. An example original gain level is 30.0 mm/mV. The term gain level, as used herein, refers to a ratio of a unit of a display band's height to a unit of a physiologic signal segment's amplitude. For example, where a unit of the display band's height is millimeters (mm), and a unit of the physiologic signal segment's amplitude is millivolts (mV), then the gain level is the ratio of mm/mV. In certain embodiments, the signal range threshold is a quotient of the specified height of the display band divided by the original gain level. In other words, the signal range threshold can be determined using the equation: signal range threshold=specified height of display band/original gain level. Continuing with the above example, where the specified height of the display band was 20 mm, and the original gain level was 30 mm/mV, then the threshold signal range=specified height of display band/original gain level=20 mm/30 mm/mV=0.67 mV.

Step 210 involves determining whether the original signal segment range (determined at step 206) is greater than the threshold signal range (determined at step 208). If the answer to the determination at step 210 is No (i.e., if the original signal segment range is not greater than the threshold signal range), then flow goes to step 212. When flow goes to step 212, that means that the original signal segment range is sufficiently narrow such that if portions of the physiologic signal segment within the original signal segment range were displayed within the display band, relatively small features of the physiologic signal segment would likely be sufficiently visible to a person (e.g., clinician). Accordingly, step 212 involves causing portions of the physiologic signal segment that are within the original signal segment range to be displayed within the display band, which should result in both the maximum and minimum peaks of the physiologic signal segment (obtained at step 202) being displayed within the display band. If the answer to the determination at step 210 is Yes (i.e., if the original signal segment range is indeed greater than the threshold signal range), then flow goes to step 214 in FIG. 2B. More generally, when flow goes to step 214, that means that the original signal segment range is sufficiently wide such that if portions of the physiologic signal segment within the original signal segment range were displayed within the display band, small features of the physiologic signal segment would likely be difficult to visualize.

Reference is now made to FIG. 2B, wherein the steps in FIG. 2B, starting with step 214, are performed when the answer to the determination at step 210 is Yes (i.e., when the original signal segment range is greater than the threshold signal range). As will be appreciated from the discussion of FIG. 2B, the steps in FIG. 2B are used to define a new display range and a new gain level, which are used to improve the visibility of small features of the physiologic signal segment when portions thereof are displayed. Steps 204 through 210, which were described above with reference to FIG. 2A, are used to selectively determine whether or not a new display range and a new gain level should be determined and used to improve the visibility of small features of the physiologic signal segment when portions thereof are displayed. In alternative embodiments, steps 204 through 212 are skipped or eliminated, and flow instead goes directly from step 202 in FIG. 2A to step 214 in FIG. 2B. In other words, in certain embodiments, regardless of the original display range and the original gain level, a new display range and a new gain level are determined for a physiologic signal segment that is obtained at an instance of step 202. More generally, steps 204 through 212 can be considered optional steps.

Referring to FIG. 2B, step 214 involves dividing the physiologic signal segment (e.g., EGM signal segment) into a plurality of sub-segments. In certain embodiments, each of the sub-segments (with the possible exception of the last sub-segment) has a predetermined duration. For example, if the duration of the physiologic signal segment (obtained at step 202) is 40 seconds, and each of the sub-segments has a predetermined duration of 4 seconds, then the physiologic signal segment is divided into 10 sub-segments. In other embodiments, rather than each of the sub-segments having a fixed duration, the physiologic signal segment is divided into a predetermined number of sub-segments. For example, if a duration of the physiologic signal segment (obtained at step 202) is 40 seconds, and the physiologic signal segment is divided into 20 sub-segments, then each of the 20 sub-segments would be 2 seconds in duration. In the above examples, the durations of the sub-segments resulting from step 204 are the same as one another. However, that need not be the case. Other manners of dividing the physiologic signal segment (e.g., EGM signal segment) into a plurality of sub-segments, besides those described above, are also within the scope of the embodiments described herein. In certain embodiments, the physiologic signal segment should be divided into at least 10 sub-segments in order for certain statistical analysis (such as inter-quartile range and/or the like) performed in later steps to be statistically meaningful.

Steps 216 through 224 in FIG. 2B are initially broadly introduced below, and then additional details of those steps are described using various example values. Step 216 involves determining a sub-segment minimum (min) peak amplitude and a sub-segment maximum (max) peak amplitude, for each of the plurality of sub-segments, to thereby determine a plurality of sub-segment minimum peak amplitudes and a plurality of sub-segment maximum peak amplitudes. Step 218 involves determining a new minimum peak amplitude based on the plurality of sub-segment minimum peak amplitudes, and a new maximum peak amplitude based on the plurality of sub-segment maximum peak amplitudes. Step 220 involves determining a new display range based on the new minimum peak amplitude and the new maximum peak amplitude. Step 222 involves determining a new gain level based on the new display range and the specified height of the display band. Step 224 involves determining a scale indicator based on the new gain level (determined at step 222) and the height of a major amplitude marker of the display band, as will be explained in more detail below.

Referring again to step 214, assume for example that step 214 resulted into the physiologic signal segment (obtained at step 202) being divided into 10 sub-segments. Also assume that the plurality of sub-segment minimum peak amplitudes (determined at step 216) are –0.2 mV, –0.25 mV, –0.15 mV, –0.2 mV, –0.2 mV, 0.1 mV, –0.25 mV, –0.8 mV, –0.6 mV and –0.2 mV; and that the plurality of sub-segment maximum peak amplitudes (determined at step 216) are 0.2 mV, 0.25 mV, 0.15 mV, 0.2 mV, 0.2 mV, 0.15 mv, 0.25 mV, 0.8 mV, 0.6 mV and 0.2 mV. As mentioned above, step 218 involves determining a new minimum peak amplitude based on the plurality of sub-segment minimum peak amplitudes, and a new maximum peak amplitude based on the plurality of sub-segment maximum peak amplitudes.

In certain embodiments, the new minimum peak amplitude is determined at step 218 by calculating a 25% quartile value of the plurality of sub-segment minimum peak amplitudes, and calculating an inter-quartile range (IQR) of the plurality of sub-segment minimum peak amplitudes. A first outlier threshold is then calculated using the equation: first outlier threshold=25% quartile value–whisker*IQR, where the whisker is set to 3 (or some other value within the range of 1 to 5). The plurality of sub-segment minimum peak amplitudes are then separated into first and second subsets thereof, such that the first subset includes each of the sub-segment minimum peak amplitudes this is less than the first outlier threshold, and the second subset includes each of the sub-segment minimum peak amplitudes that is not less than the first outlier threshold. A first candidate for being the new minimum peak amplitude is determined based on the first subset of the plurality of sub-segment minimum peak amplitudes, and a second candidate for being the new minimum peak amplitude is determined based on the second subset of the plurality of sub-segment minimum peak amplitudes. A minimum of the first and second candidates for being the new minimum peak amplitude is then selected as the new minimum peak amplitude.

In certain embodiments, the first candidate for being the new minimum peak amplitude is determined by calculating a mean (or median, or maximum, or minimum) of the first subset of the plurality of sub-segment minimum peak amplitudes, and multiplying the mean (or median, or maximum, or minimum) by a truncation value. An example truncation value is 70%, but the use of other truncation values is also possible and within the scope of the embodiments described herein. In certain embodiments, the second candidate for being the new minimum peak amplitude is determined by determining a minimum of the second subset of the plurality of sub-segment minimum peak amplitudes.

Continuing with the example introduced above, where the plurality of sub-segment minimum peak amplitudes (determined at step 216) are –0.2 mV, –0.25 mV, –0.15 mV, –0.2 mV, –0.2 mV, 0.1 mV, –0.25 mV, –0.8 mV, –0.6 mV and –0.2 mV, the following would be the results of the above described calculations and determinations that are used to determine the new minimum peak amplitude:

75% quartile=–0.2 mV

25% quartile=–0.25 mV

IQR=75% quartile–25% quartile=–0.2–(–0.25)=0.05 mV

First outlier threshold=25% quartile–3*IQR=–0.25–3*0.05=–0.4 mV $V$min values<first outlier threshold: [–0.8,–0.6]

$V$min values>=first outlier threshold=[–0.2,–0.25,–0.15,–0.2,–0.2,0.1,–0.25,–0.2]

1$^{st}$ candidate new min peak amp=70%*mean([–0.8,–0.6])=70%*(–0.7)=–0.49 mV

2$^{nd}$ candidate new min peak amp=min([–0.2,–0.25,–0.15,–0.2,–0.2, 0.1,–0.25,–0.2])=–0.25 mV New min peak amp=min[–0.49,–0.25]=–0.49 mV In certain embodiments, the new maximum peak amplitude is determined at step 218 by calculating a 75% quartile value of the plurality of sub-segment maximum peak amplitudes, and calculating an inter-quartile range (IQR) of the plurality of sub-segment maximum peak amplitudes. A second outlier threshold is then calculated using the equation: second outlier threshold=75% quartile value–whisker*IQR, where the whisker is set to 3 (or some other value within the range of 1 to 5). The plurality of sub-segment maximum peak amplitudes are then separated into first and second subsets thereof, such that the first subset includes each of the sub-segment maximum peak amplitudes this is greater than the second outlier threshold, and the second subset includes each of the sub-segment minimum peak amplitudes that is not greater than the second outlier threshold. A first candidate for being the new maximum peak amplitude is determined based on the first subset of the plurality of sub-segment maximum peak amplitudes, and a second candidate for being the new maximum peak amplitude is determined based on the second subset of the plurality of sub-segment maximum peak amplitudes. A maximum of the first and second candidates for being the new maximum peak amplitude is then selected as the new maximum peak amplitude.

In certain embodiments, the first candidate for being the new maximum peak amplitude is determined by calculating a mean (or median, or maximum, or minimum) of the first subset of the plurality of sub-segment maximum peak amplitudes, and multiplying the mean (or median, or maximum, or minimum) by a truncation value. An example truncation value is 70%, but the use of other truncation values is also possible and within the scope of the embodiments described herein. In certain embodiments, the second candidate for being the new maximum peak amplitude is determined by determining a maximum of the second subset of the plurality of sub-segment maximum peak amplitudes.

Continuing with the example introduced above, where the plurality of sub-segment maximum peak amplitudes (determined at step 216) are 0.2 mV, 0.25 mV, 0.15 mV, 0.2 mV, 0.2 mV, 0.15 mv, 0.25 mV, 0.8 mV, 0.6 mV and 0.2 mV, the following would be the results of the above described calculations and determinations that are used to determine the new maximum peak amplitude:

75% quartile=0.25 mV

25% quartile=0.2 mV

IQR=75% quartile–25% quartile=0.25–0.2=0.05 mV

Second outlier threshold=75% quartile+3*IQR=0.25+3*0.05=0.4 mV $V$max value>second outlier threshold: [0.8, 0.6]

$V$max values<=second outlier threshold=[0.2, 0.25, 0.15, 0.2, 0.2, 0.15, 0.25, 0.2]

1$^{st}$ candidate new max peak amp=70%*mean([0.8, 0.6])=70%*0.7=0.49 mV $2^{nd}$ candidate new max peak amp=max([0.2, 0.25, 0.15, 0.2, 0.2, 0.15, 0.25, 0.2])=0.25 mV New max peak amp=max[0.49,0.25]=0.49 mV.

In alternative embodiments, other types of statistical measures besides 75% quartile, 25% quartile and IQR may be used to determine the first and second outlier thresholds. For example, in certain embodiments the first outlier threshold is determined by calculating a mean and a standard deviation (SD) of the plurality of sub-segment minimum peak amplitudes. The first outlier threshold is then determined based on the mean and the SD of the plurality of sub-segment minimum peak amplitudes, e.g., using the equation: first outlier threshold=mean-(scale factor)*SD, wherein the scale factor is set to 3 (or another value between 1 and 5). Similarly, the second outlier threshold can be determined by calculating a mean and a standard deviation (SD) of the plurality of sub-segment maximum peak amplitudes, and determining the second outlier threshold based on the mean and the SD of the plurality of sub-segment maximum peak amplitudes, e.g., using the equation: second outlier threshold=mean+(scale factor)*SD, wherein the scale factor is set to 3 (or another value between 1 and 5). Other variations are also possible and within the scope of the embodiments described herein.

Continuing with the above example, the new minimum peak amplitude determined at step 218 is -0.49 mV, and the new maximum peak amplitude determined at step 218 is 0.49 mV. At step 220 the new display range is determined as being from the new minimum peak amplitude of -0.49 mV to the new maximum peak amplitude of 0.49 mV, and thus, the new display range determined at step 220 is 0.98 mV. This is in contrast to an original display range of 1.6 mV (i.e., from -0.8 mV to 0.8 mV) for the physiologic signal segment (obtained at step 202).

At step 222 the new gain level is determined based on the new display range and the specified height of the display band, e.g., using the equation: new gain level=specified height of the display band/new display range. Assuming, for example, that the specified height of the display band is 20 mm, and continuing with the above example of the new display ranging being 0.98 mV, the new gain level=20 mm/0.98 mV=20.4 mm/mV. As noted above, the term gain level, as used herein, refers to a ratio of a unit of a display band's height to a unit of a physiologic signal segment's amplitude. For example, where a unit of the display band's height is a millimeters (mm), and a unit of the physiologic signal segment's amplitude is millivolts (mV), then the gain level is the ratio of mm/mV. In the embodiments described herein, the greater the new gain level, the more the portion of the physiologic signal segment (caused to be displayed within the display band having the specified height at step 226) will appear as if it has been magnified. Accordingly, the greater the new gain level, the easier it will be for a clinician or other individual to be able to visualize relatively small features of the physiologic signal segment. For example, where the physiologic signal segment is an EGM or ECG signal segment, the greater the new gain level, the easier it will be for a clinician to visualize P-waves of the EGM or ECG signal segment. However, the corollary is that the greater the new gain level, potentially the smaller the portion of the physiologic signal segment (in terms of amplitude) that is displayed within the display band. This is analogous to increasing the gain level of a microscope being used to visualize a sample, in that increasing the gain level of the microscope has the effect magnifying the features of the sample that can be seen through the eyepiece of the microscope, while decreasing the area of the sample that can be seen through the eyepiece of the microscope.

At step 224 the scale indicator is determined based on the new gain level and the height of a major amplitude marker of the display band, e.g., using the equation: scale indicator=height of a major amplitude marker of display band/new gain level. The height of a major amplitude marker of the display band is the distance between major amplitude markers of the display band, and thus, can be equal to the height of the display band divided by the number of major amplitude markers. For example, where the height of the display band is 20 mm, and there are 4 major amplitude markers, then the height of a major amplitude marker of the display band=20 mm/4=5 mm. Continuing with this example, where the height of the major amplitude marker of the display band is 5 mm, and the new gain level is 20.4 mm/mV, then the scale indicator=5 mm/20.4 mm/mV=0.25 mV. In this example, the number of major amplitude markers (which include the upper and lower boundaries of the display band) was an integer (i.e., 4), however that need not be the case. For another example, the number of major amplitude markers could be 4.5, in which case the height of a major amplitude marker of the display band=20 mm/4.5=4.44 mm, and the scale indicator=4.44 mm/20.4 mm/mV=0.22 mV.

Still referring to FIG. 2B, step 226 involves causing displaying, within the display band (e.g., 404 in FIG. 4) having the specified height, of a portion of the physiologic signal segment that is within the new display range, such that the upper boundary (e.g., 405 in FIG. 4) of the display band corresponds to the new maximum peak amplitude, and the lower boundary (e.g., 406 in FIG. 4) of the display band corresponds to the new minimum peak amplitude.

Still referring to FIG. 2B, step 228 involves causing further displaying, within or proximate to the display band having the specified height, of at least one of the new gain level, the scale indicator determined based on the new gain level, or a surrogate of the scale indicator. Displaying such one or more values within or proximate to the display band enables someone (e.g., a clinician) viewing the display band to discern magnitudes of the features of the physiologic signal segment that are being displayed within the display band. Examples of how the new gain level, the scale indicator, and/or a surrogate of the gain indicator may be displayed within or proximate to the display band are described below with reference to FIG. 4. Following step 228, flow returns to step 202 in FIG. 2A, where another (e.g., a next) physiologic signal segment is obtained, and the remaining steps are repeated. Similarly, flow could return to step 202 following step 212, as was shown in FIG. 2A.

Figure 3:
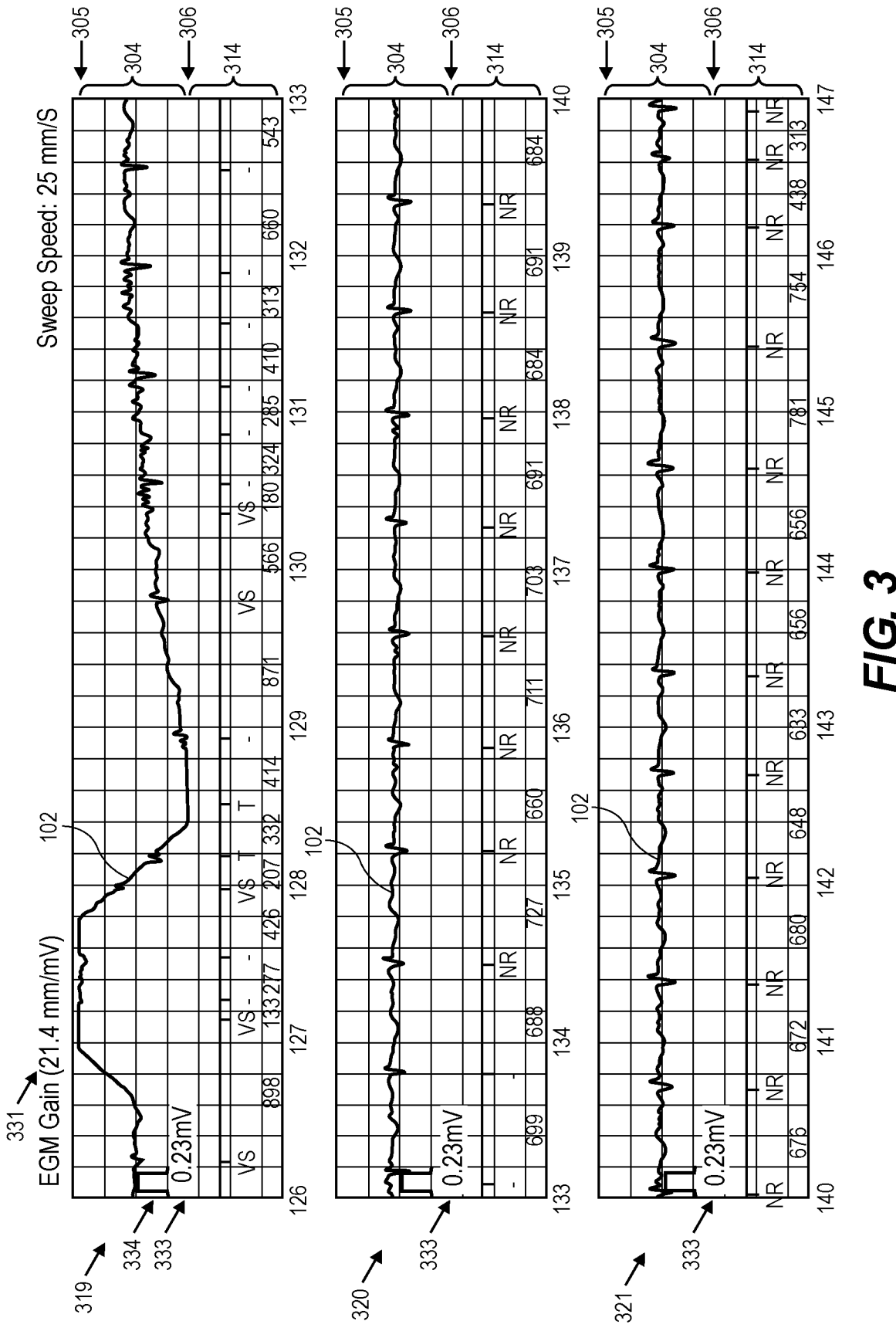
FIG. 3 shows three examples of panels of a display band including portions of an EGM signal segment that may be displayed to a clinician, wherein small signal components of the EGM signal segment are difficult to visualize, if they can be visualized at all.
Figure 4:
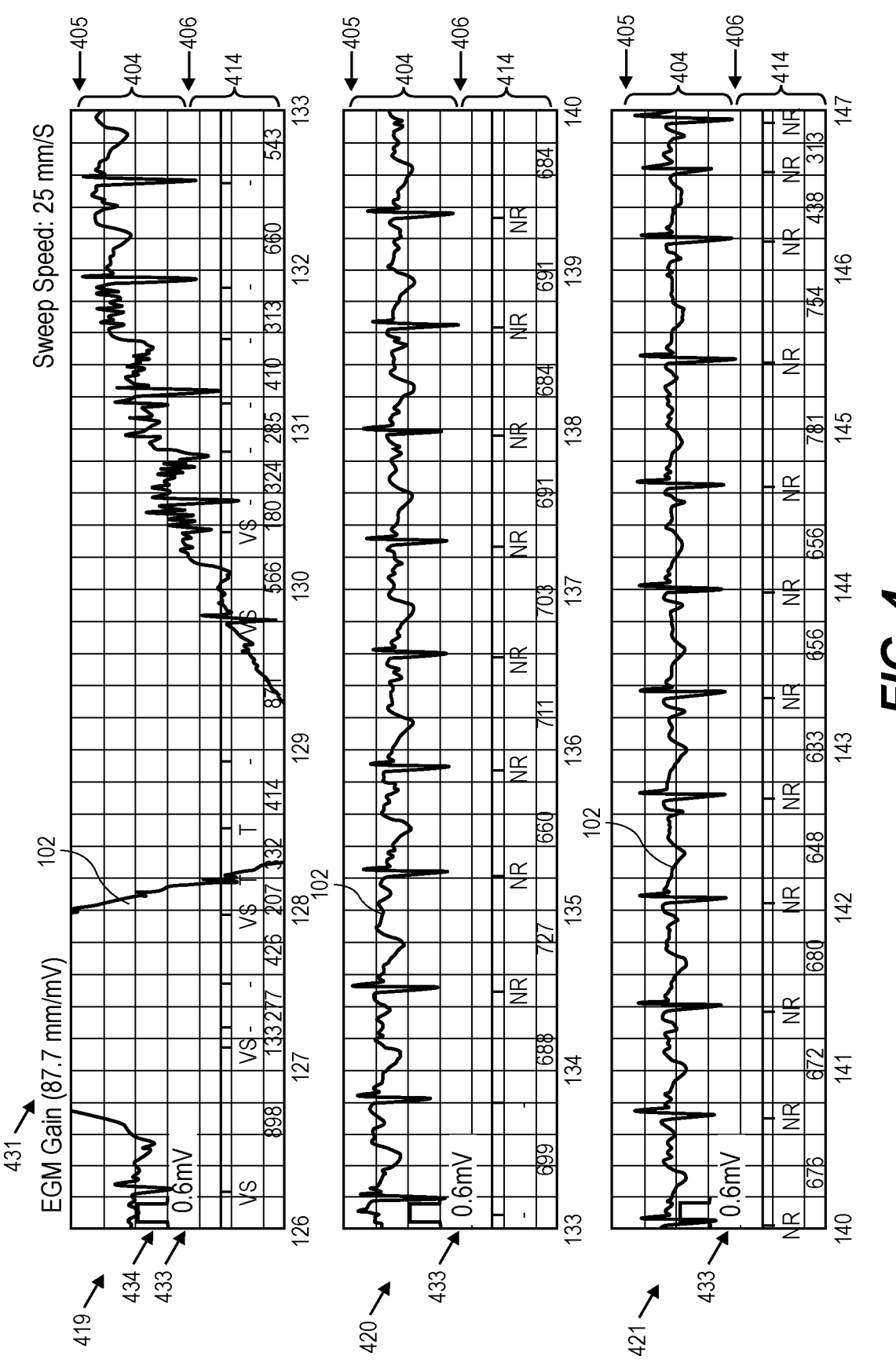
FIG. 4 shows three examples of panels of a display band including portions of an EGM signal segment that may be displayed to a clinician, using an embodiment of the present technology that improves the visualization of small signal components of the EGM signal segment.

FIGS. 3 and 4 will now be used to show and describe how an embodiment of the present technology, summarized above with reference to the flow diagram of FIG. 2 (which includes FIGS. 2A and 2B), can be used to improve the visibility of features of a physiologic signal segment, and more specifically an EGM signal segment, that is displayed within a display band having a specified height. When discussing FIGS. 3 and 4, reference will be made back to the EGM signal segment 102 originally shown in FIG. 1, as well as some of the steps described above with reference to FIG. 2.

Referring briefly back to FIG. 1, the duration of the EGM signal segment 102 shown therein is 150 seconds. When such an EGM signal segment is displayed to a clinician, it is typically broken down into panels that are shown one above the other on a display monitor, touchscreen, printout, and/or the like. Such panels may each have a specified duration, such as 7 seconds. FIG. 3 shows three examples of such panels that may be displayed to a clinician, such that maximum and minimum peaks of the EGM signal segment, within a dynamic range of –0.4 mV to +0.4 mV that has been specified by the clinician using a user interface. More specifically, referring to FIG. 3, three panels 319, 320 and 321 are shown therein, wherein the uppermost panel 319 corresponds to a portion of the EGM signal segment 102 from 126 seconds to 133 seconds, the middle panel 320 corresponds to a portion of the EGM signal segment 102 from 133 seconds to 140 seconds, and the lowermost panel 321 corresponds to a portion of the EGM signal segment 102 from 140 seconds to 147 seconds. Additional panels corresponding to portions of the EGM signal segment 102 from 0 seconds to 126 seconds and/or from 147 seconds to 150 seconds may also be displayed, but are not shown herein. Each of the panels 319, 320, 321 includes a display band portion 304 having a specified height between an upper boundary 305 and a lower boundary 306 of the display band 304, and a marker band portion 314 that is displayed below the display band portion 304. The display band portions 304 can be collectively referred to as the display band 304, and the marker band portions 314 can be collectively referred to as the marker band 314. It is presumed for this example that the specified height of the display band 304 is 18 mm. The specified height of the display band can be fixed. Alternatively, the specified height of the display band may be adjustable, e.g., selectable by a user (e.g., a clinician) via a user interface. As can be appreciated from FIG. 3, the EGM signal segment 102 is displayed within the display band 304, and marker symbols (e.g., VS, T, and NR) are displayed within the marker band 314. For examples, the marker symbol VS indicates a Ventricular Sensed event, the marker symbol NR indicates a Ventricular Sensed event during Noise Recovery, and the marker symbol T indicates a Ventricular Sensed event which satisfies a tachycardia interval binning criteria. Additional and/or alternative marker symbols may be displayed within the marker band 314. Also shown in FIG. 3 is gain level value 331 and a scale indicator value 333. The gain level value 331 was determined using the equation: gain level=specified height of the display band/display range=18 mm/0.84 mV=21.4 mm/mV. The scale indicator value 333 was determined using the equation: scale indicator=the height of a major amplitude marker of the display band/gain level=5 mm/21.4 mm/mV=0.23 mV. Each display band unit is represented as a square within the display band. Above the scale indicator value 333 (of 0.23 mV) is shown a square wave 334, which is intended to show that the height of the square wave 334 corresponds to 0.23 mV (i.e., corresponds to the scale indicator value 333).

As can be appreciated from FIG. 3, because of the large peaks in the EGM signal segment from about 127 to 128 seconds, which caused the original signal range to be relatively large, features (aka components) of the remaining portions of the EGM signal segment appear rather small within the display band 304. More specifically, while QRS complexes (corresponding to ventricular depolarizations) can typically be visualized within the display band 304, P-waves (corresponding to atrial depolarizations) are very difficult to visualize within the display band 304, if they can be seen at all. Accordingly, if a clinician were to view the EGM signal segment within the display band 304 for the purpose of analyzing atrial activity of a patient, the display band 304 would be difficult to analyze. This is because, as noted above, the display range of the EGM signal segment 102 introduced in FIG. 1 is relatively large.

FIG. 4 shows three panels 419, 420 and 421 that may be displayed in place of the panels 319, 320 and 321 described above with reference to FIG. 3. The uppermost panel 419 corresponds to a portion of the EGM signal segment 102 from 126 seconds to 133 seconds, the middle panel 420 corresponds to a portion of the EGM signal segment 102 from 133 seconds to 140 seconds, and the lowermost panel 421 corresponds to a portion of the EGM signal segment 102 from 140 seconds to 147 seconds. Additional panels corresponding to portions of the EGM signal segment 102 from 0 seconds to 126 seconds and/or from 147 seconds to 150 seconds may also be displayed, but are not shown herein. Each of the panels 419, 420, 421 includes a display band portion 404 having a specified height between an upper boundary 405 and a lower boundary 406 of the display band 404, and a marker band portion 414 that is displayed below the display band portion 304. The display band portions 404 can be collectively referred to as the display band 404, and the marker band portions 414 can be collectively referred to as the marker band 414. As was the case in FIG. 3, it is again presumed for this example that the specified height of the display band 404 is 18 mm. As noted above, the specified height of the display band can be fixed, or can be adjustable, e.g., selectable by a user (e.g., a clinician) via a user interface.

The EGM signal segment displayed within the display band 404 in FIG. 4 was caused to be displayed using an embodiment of the present technology described above with reference to the flow diagram of FIG. 2. The table in FIG. 5 is used to describe how the EGM signal segment displayed within the display band 404 in FIG. 4 was caused to be displayed. Initially, the EGM signal segment 102 (in FIG. 1) was divided into 37 sub-segments that were each 4 seconds in duration, at step 214 in FIG. 2. Referring briefly back to FIG. 1, the vertical dotted lines illustrate how the EGM signal segment 102 can be divided into 37 sub-segments that are each 4 seconds in duration. In the table of FIG. 5, each of the rows corresponds to a respective one of the sub-segments that are labeled numbers (nos.) 1 to 37 in the first column of FIG. 5. Next, at step 216, a sub-segment minimum peak amplitude and a sub-segment maximum peak amplitude was determined, for each of the sub-segments, to thereby produce a plurality of sub-segments minimum peak amplitudes and a plurality of sub-segment maximum peak amplitudes, which values are shown in the third and second columns in FIG. 5. A new minimum peak amplitude of –0.1099 mV and a new maximum peak amplitude of 0.0952 mV were then determined at step 218 in FIG. 2. The new display range was then determined at step 220 using the equation new display range=new maximum peak amplitude–new minimum peak amplitude=0.0952 mV–(–0.1099 mV)=0.2051 mV. The new gain level was then determined at step 222 using the equation: new gain level=specified height of the display band/new display range=18 mm/0.2051 mV=87.7 mm/mV. The new gain level (of 87.7 mm/mV) is shown as the gain level value 431 in FIG. 4. The scale indicator was then determined at step 224 using the equation: scale indicator=the height of a major amplitude marker of the display band/new gain level=5 mm/87.7 mm/mV=0.06 mV. The scale indicator (of 0.06 mV) is shown as the scale indicator value 433 in FIG. 4, just below the square wave 334, which is intended to show that the height of the square wave 434 corresponds to 0.06 mV (i.e., corresponds to the scale indicator value 433). Alternatively, or additionally, a surrogate of the scale indicator can be incremental amplitude values along a vertical axis of the display band 404 (e.g., the value of the new minimum peak amplitude can be displayed at or adjacent to the lower boundary 406 of the display band 404, and the value of the new maximum peak amplitude can be displayed at or adjacent to the upper boundary 405 of the display band 404). Referring again to FIG. 5, the sub-segment maximum peak amplitude values that correspond to sub-segments 32-37 are greater than the Vmax outlier threshold of 0.0567 mV, and are examples of outliers. Still referring to FIG. 5, the sub-segment minimum peak amplitude values that correspond to sub-segments 32-37 are less than the Vmin outlier threshold of −0.0756 mV, and are further examples of outliers.

As can be appreciated from a comparison between FIG. 3 and FIG. 4, features (aka components) of the EGM signal segment appear larger in FIG. 4 within the display band 404. More specifically, in addition to QRS complexes (corresponding to ventricular depolarizations) being easily visualized within the display band 404, P-waves (corresponding to atrial depolarizations) can also be easily visualized within the display band 404. Accordingly, if a clinician were viewing the EGM signal segment within the display band 404 for the purpose of analyzing atrial activity of a patient, the display band 404 would be easier to analyze than the display band 304. This is in part because the new display range is relatively narrow compared to the original display range.

In certain embodiments, an example of which is shown in the uppermost panel 419 in FIG. 4, a lower portion of the physiologic signal segment (e.g., 102) that is displayed is allowed to extend beyond the lower boundary 406 of the display band 404, such the lower portion of the physiologic signal segment extends into and overlaps the marker band 414. In other embodiments, no portion of the physiologic signal segment that is displayed extends below the lower boundary 406 of the display band 404.

As noted above, step 202 involves obtaining a physiologic signal segment indicative of physiologic activity of a patient for a period of time that includes a plurality of cycles of the physiologic activity. As also noted above, the physiologic signal segment can be indicative of cardiac electrical activity of the patient for a period of time that includes a plurality of cardiac cycles. The physiologic signal segment that is indicative of cardiac electrical activity can be, e.g., an electrogram (EGM) or electrocardiogram (ECG) signal segment. In certain embodiments, the EGM or ECG signal segment is stored in memory in response to an arrhythmic episode being detected by an implanted or non-implanted device, so that that the EGM or ECG signal segment can be viewed and analyzed by a clinician. Embodiments of the present technology enable relatively small signal components, such as P-waves indicative of atrial depolarizations, to be more readily observed (i.e., to be more visible to a clinician) when a portion of the signal segment is displayed.

The physiologic signal segment obtained at step 202 can alternatively be indicative of cardiac mechanical activity of the patient for a period of time that includes a plurality of cardiac cycles. The physiologic signal segment that is indicative of cardiac mechanical activity can be, e.g., a photoplethysmography (PPG) signal segment, an impedance plethysmography (IPG) signal segment, or a heart sounds signal, but is not limited thereto. Such a PPG signal segment can be sensed using a PPG sensor, which is a type of optical sensor that can be an implantable sensor or a non-implantable (aka external) sensor. As will be described in additional detail below, an IPG signal segment can be sensed using two or more electrodes and impedance measurement circuitry. A heart sounds signal can be sensed, e.g., using a microphone, accelerometer, or a piezoelectric element. The physiologic signal segment obtained at step 202 can alternatively be indicative of respiratory activity of the patient for a period of time that includes a plurality of respiratory cycles. These are just a few examples of the types of physiologic signal segments that can be obtained at step 202, which examples are not intended to be all encompassing.

Embodiments of the present technology, which were summarized above with reference to the flow diagram of FIG. 2, automatically identify outlier peaks of a physiologic signal segment and adjust a display range (from an original display range to a new display range) to provide for better visibility of relatively small features (aka components) of the physiologic signal segment. Such outlier peaks are identified by performing steps 214, 216 and 218, and then a distribution of the peaks of the physiologic signal segment is analyzed at step 220, to determine the new display range. If no outlier peaks are found, then the display range may be unchanged, and an entirety original signal range of the physiologic signal segment may be displayed within the display band. However, when outliers are identified, a new display range and a new gain level are determined and used to improve the visibility of relatively small features of a portion of the physiologic signal segment displayed within the display band.

Example Implantable Medical Device

Figure 6:
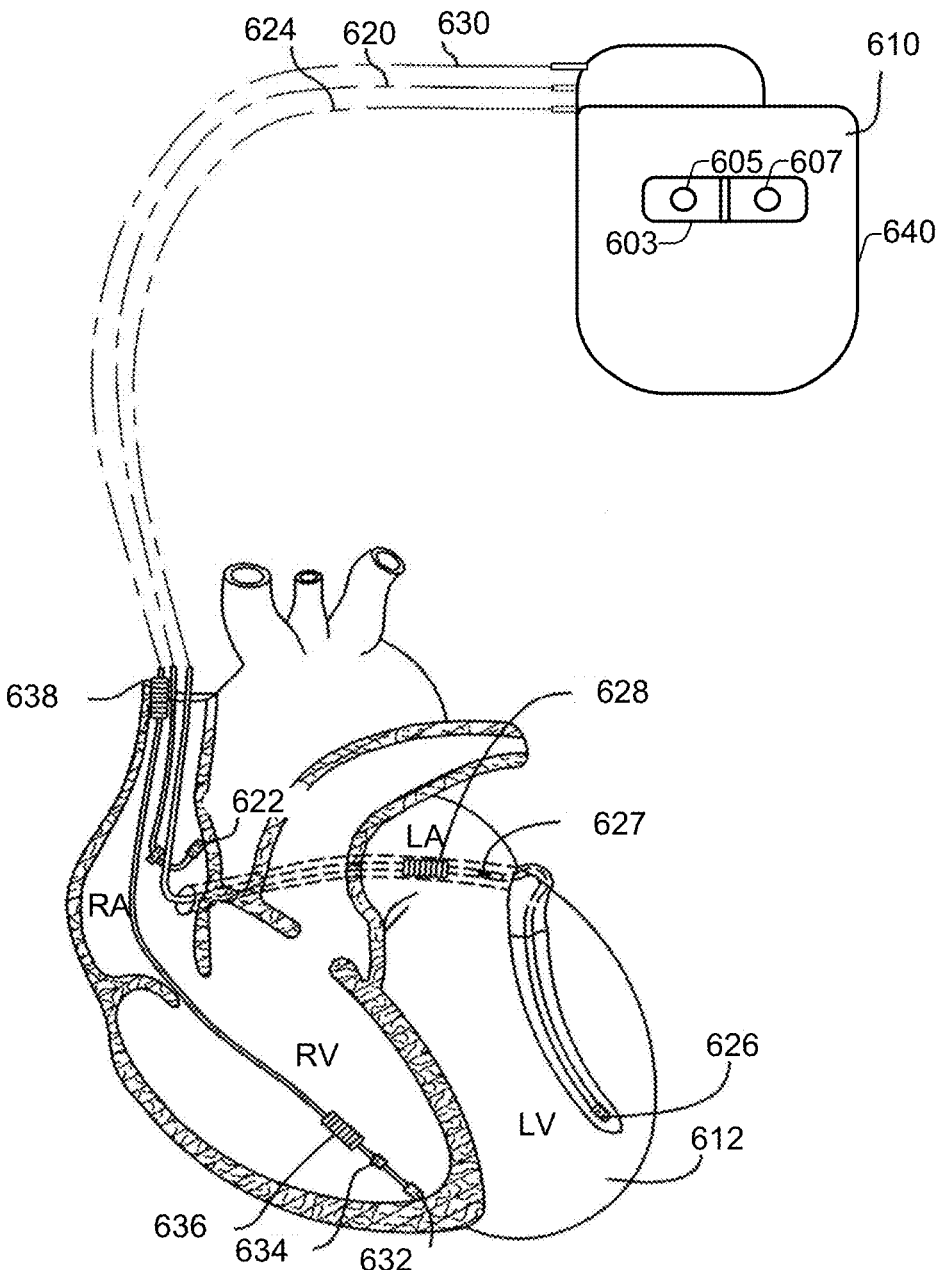
FIG. 6 illustrates an example IMD that can be used to sense and store physiologic signal segments that are thereafter transmitted to an external system that displays one of more of the physiologic signal segments, or one or more portion(s) thereof, in accordance with certain embodiments of the present technology.
Figure 7:
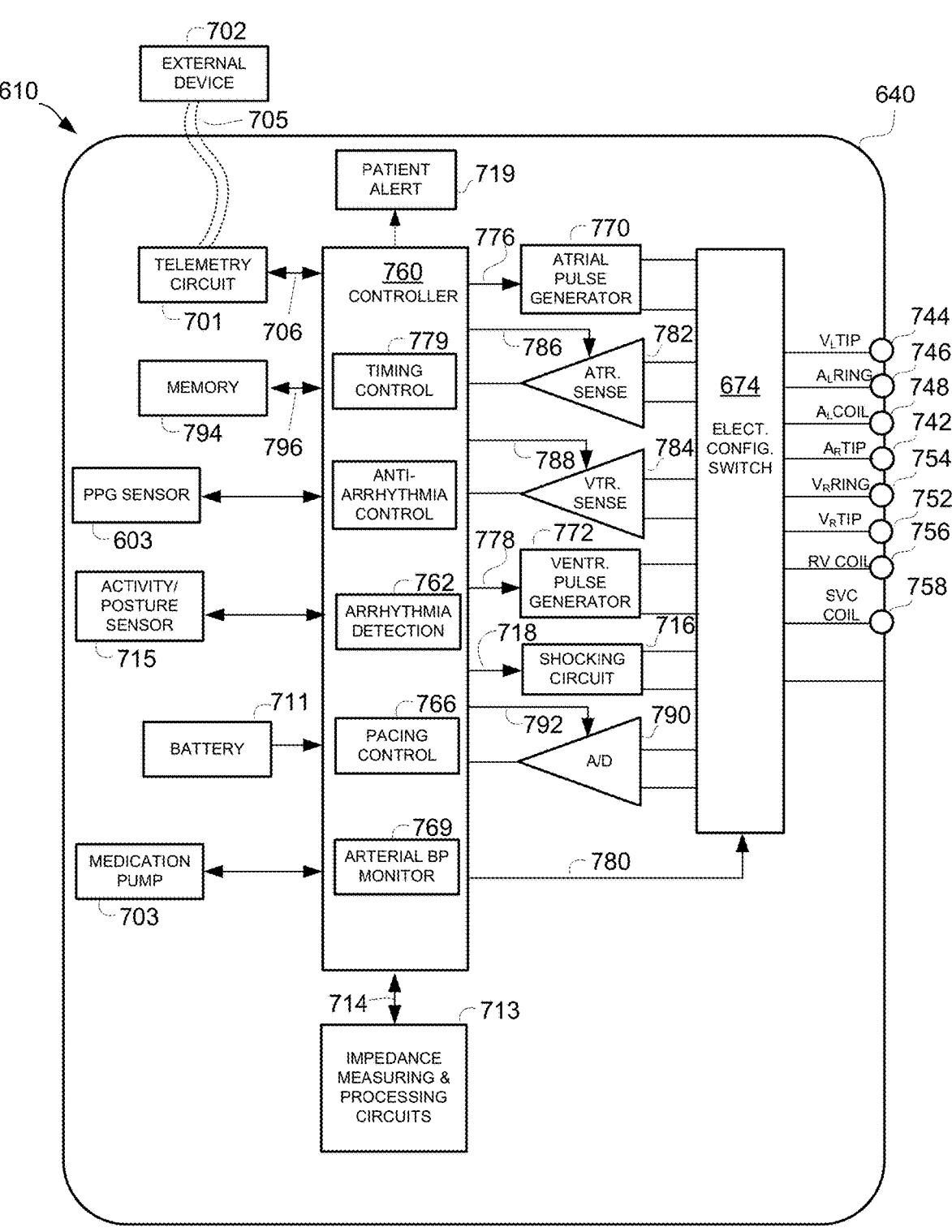
FIG. 7 illustrates example details of the components of the IMD introduced in FIG. 6.

The physiologic signal segments obtained at instances of step 202 of FIG. 2 can be sensed and stored by an implantable medical device (IMD) and then transmitted or otherwise uploaded to a non-implanted system that can display and/or analyze at least some portions of at least some of the physiologic signal segments. For example, EGM signal segments may be displayed to a clinician so that the clinician can view and analyze one or more EGM signal segments. FIGS. 6 and 7 illustrate an example of an IMD that can be used to sense and store physiologic signal segments, such as EGM signal segments, PPG signal segments, IPG signal segments, heart sound signal segments, and/or the like.

FIG. 6 illustrates an IMD 610, which can be a pacing device and/or an implantable cardioverter defibrillator (ICD). The IMD 610 is shown as being in electrical communication with a patient's heart 612 by way of three leads, 620, 624 and 630, which can be suitable for delivering multi-chamber stimulation and shock therapy. The leads can also be used to obtain EGM signals, for use in embodiments of the present technology. As described below, it is also possible that one of these leads (or another lead) can include an optical sensor (also referred to as a PPG sensor) that is useful for obtaining a PPG signal.

In FIG. 6, the IMD 610 is shown as having a PPG sensor 603 (also referred to as an optical sensor) attached to its housing 640. The PPG sensor 603, which can be used to obtain a PPG signal, includes a light source 605 and a light detector 607. The light source 605 can include, e.g., at least one light-emitting diode (LED), incandescent lamp or laser diode, but is not limited thereto. The light detector 607 can include, e.g., at least one photoresistor, photodiode, phototransistor, photodarlington or avalanche photodiode, but is not limited thereto. Light detectors are often also referred to as photodetectors or photocells.

The light source 605 outputs light that is reflected or backscattered by surrounding patient tissue, and reflected/backscattered light is received by the light detector 607. In this manner, changes in reflected light intensity are detected by the light detector 607, which outputs a signal indicative of the changes in detected light. The output of the light detector 607 can be filtered and amplified. The signal can also be converted to a digital signal using an analog to digital converter, if the PPG signal is to be analyzed in the digital domain. A PPG sensor can use a single wavelength of light, or a broad spectrum of many wavelengths. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The extravascular PPG sensor 602 can be attached to a housing 640 of an implantable device, which as mentioned above can be, e.g., a pacemaker and/or an ICD. Exemplary details of how to attach a sensor module to an implantable cardiac stimulation device are described in U.S. Pat. No. 7,653,434, entitled "Autonomous Sensor Modules for Patient Monitoring" (Turcott et al.), which is incorporated herein by reference. It is also possible that the PPG sensor 602 be integrally part of the implantable cardiac stimulation device 610. For example, the PPG sensor 602 can be located within the housing 640 of an ICD (and/or pacemaker) that has a window through which light can be transmitted and detected. In a specific embodiment, the PPG sensor 602 has a titanium frame with a light transparent quartz or sapphire window that can be welded into a corresponding slot cut in the housing of the ICD. This will ensure that the ICD enclosure with the welded PPG sensor will maintain a hermetic condition.

Where the PPG sensor is incorporated into or attached to a chronically implantable device 610, the light source 605 and the light detector 607 can be mounted adjacent to one another on the housing or header of the implantable device, or on the bottom of the device, or at any other location. The light source 605 and the light detector 607 can be placed on the side of the implantable device 610 that, following implantation, faces the chest wall, and are configured such that light cannot pass directly from the source to the detector. The placement on the side of the device 610 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 605 and the light detector 607 can be placed on the face of the device 610 that faces the skin of the patient. Other variations are also possible.

In an alternative embodiment, the PPG sensor 603 (or other plethysmography sensor) is remote from the housing 640 of the device 610, but communicates with the electronics in the device housing 640 via one or more wires, optical fibers, or wirelessly (e.g., using telemetry, RF signals and/or using body fluid as a communication bus medium). This embodiment enables an obtained PPG signal to be indicative of changes in arterial blood volume at a location remote from the patient's heart, where such location is also remote from the device housing 640. If desired, multiple PPG signals can be obtained, e.g., using multiple PPG sensors at different locations.

In another embodiment, optical fibers can be used to transmit light into and detect light from tissue that is remote from the device housing, even though the light source and light detector are located within or adjacent the device housing 640. This embodiment enables an obtained PPG signal to be indicative of changes in arterial blood volume at a location remote from the patient's heart, where such location is remote from the device housing 640, even though the light source 605 and light detector 607 are not remote from the housing. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

In an embodiment, a PPG sensor can be within or attached to a lead that may extend from a main device housing 640. Accordingly, in this embodiment, a housing of the sensor module is sized to fit within the implantable lead. For example, the PPG can be located proximally from the distal tip of the lead so that the PPG sensor is sufficiently remote from the heart that variations in pulse transmission time are detectable and meaningful. The portion of the lead that is adjacent to a window of the PPG sensor module, where light is to exit and enter, should allow the light to pass in and out of the sensor. Thus, the lead may be transparent, or include its own window, opening, or the like. The lead can include tines for attaching the lead in its desired position, but may include any other type of fixation means (e.g., a pigtail shaped fixation means), or none at all. The lead can also have a suture sleeve, that enables the lead to be sutured to patient tissue. Additional details of a lead that includes an optical sensor that can be used to produce a PPG signal are provided in U.S. Pat. No. 7,660,616, entitled "Improved Multi-Wavelength Implantable Oximeter Sensor" (Poore), and U.S. Pat. No. 7,840,246, entitled "Implantable Device with a Calibration Photodetector" (Poore), which are incorporated herein by reference.

For much of the above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present technology should not be limited to use with PPG sensors and PPG signals. For example, electrodes of the various leads discussed below can be used to obtain an IPG signal, of which one or more segments can be stored. Details of exemplary implantable sensors that produce an impedance plethysmography signals are disclosed, e.g., in U.S. Pat. Nos. 4,674,518, 4,686,987 and 5,334,222 (all to Salo), which are incorporated herein by reference.

Still referring to FIG. 6, to sense atrial cardiac signals and to provide right atrial chamber stimulation therapy, the device 610 is coupled to an implantable right atrial lead 620 having at least an atrial tip electrode 622, which typically is implanted in the patient's right atrial appendage. To sense left atrial and ventricular cardiac signals and to provide left-chamber pacing therapy, the device 610 is coupled to a "coronary sinus" lead 624 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628.

The device 610 is also shown in electrical communication with the patient's heart 612 by way of an implantable right ventricular lead 630 having, in this embodiment, a right ventricular tip electrode 632, a right ventricular ring electrode 634, a right ventricular (RV) coil electrode 636, and an SVC coil electrode 638. Typically, the right ventricular lead 630 is transvenously inserted into the heart 612 so as to place the right ventricular tip electrode 632 in the right ventricular apex so that the RV coil electrode 636 will be positioned in the right ventricle and the SVC coil electrode 638 will be positioned in the superior vena cava. Accordingly, the right ventricular lead 630 is capable of receiving cardiac signals and delivering stimulation in the form of pacing and shock therapy to the right ventricle.

FIG. 7 will now be used to provide some exemplary details of the components of the implantable devices 610. Referring now to FIG. 7, the implantable devices 610, and alternative versions thereof, can include a microcontroller 760. As is well known in the art, the microcontroller 760 typically includes a microprocessor, or equivalent control circuitry, and can further include RAM and/or ROM memory, logic and timing circuitry, state machine circuitry and/or I/O circuitry. Typically, the microcontroller 760 includes the ability to process or monitor input signals (data) as controlled by a program code stored in a designated block of memory. The details of the design of the microcontroller 760 are not critical to the present technology. Rather, any suitable microcontroller 760 can be used to carry out the functions described herein. The use of microprocessor-based control circuits for performing timing and data analysis functions are well known in the art. In specific embodiments of the present technology, the microcontroller 760 performs some or all of the steps associated with determining estimating changes in arterial blood volume and changes therein, and controlling response thereto.

Representative types of control circuitry that may be used with embodiments of the present technology include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 610 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 640, shown schematically in FIG. 7, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 can further include a connector (not shown) having a plurality of terminals, 742, 744, 746, 748, 752, 754, 756, and 758 (shown schematically and, for convenience, the names of the electrodes to which they are connected are shown next to the terminals). As such, to achieve right atrial sensing and pacing, the connector includes at least a right atrial tip terminal (AR TIP) 742 adapted for connection to the atrial tip electrode 622.

To achieve left atrial and ventricular sensing, pacing and shocking, the connector includes at least a left ventricular tip terminal (VL TIP) 744, a left atrial ring terminal (AL RING) 746, and a left atrial shocking terminal (AL COIL) 748, which are adapted for connection to the left ventricular tip electrode 626, the left atrial ring electrode 627, and the left atrial coil electrode 628, respectively.

To support right ventricle sensing, pacing and shocking, the connector further includes a right ventricular tip terminal (VR TIP) 752, a right ventricular ring terminal (VR RING) 754, a right ventricular shocking terminal (RV COIL) 756, and an SVC shocking terminal (SVC COIL) 758, which are adapted for connection to the right ventricular tip electrode 632, right ventricular ring electrode 634, the RV coil electrode 636, and the SVC coil electrode 638, respectively.

An atrial pulse generator 770 and a ventricular pulse generator 772 generate pacing stimulation pulses for delivery by the right atrial lead 620, the right ventricular lead 630, and/or the coronary sinus lead 624 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators, or shared pulse generators. The pulse generators, 770 and 772, are controlled by the microcontroller 760 via appropriate control signals, 776 and 778, respectively, to trigger or inhibit the stimulation pulses.

The microcontroller 760 further includes timing control circuitry 779 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, etc.) by selectively closing the appropriate combination of switches (not shown) as is known in the art.

Atrial sensing circuits 782 and ventricular sensing circuits 784 may also be selectively coupled to the right atrial lead 620, coronary sinus lead 624, and the right ventricular lead 630, through the switch 774 for detecting the presence of cardiac activity in each of the four chambers of the heart. Accordingly, the atrial (ATR. SENSE) and ventricular (VTR. SENSE) sensing circuits, 782 and 784, may include dedicated sense amplifiers, multiplexed amplifiers, or shared amplifiers. The switch 774 determines the "sensing polarity" of the cardiac signal by selectively closing the appropriate switches, as is also known in the art. In this way, the clinician may program the sensing polarity independent of the stimulation polarity.

Each sensing circuit, 782 and 784, preferably employs one or more low power, precision amplifiers with programmable gain and/or automatic gain control, band-pass filtering, and a threshold detection circuit, as known in the art, to selectively sense the cardiac signal of interest. The automatic gain control enables the device 610 to deal effectively with the difficult problem of sensing the low amplitude signal characteristics of atrial or ventricular fibrillation. Such sensing circuits, 782 and 784, can be used to determine cardiac performance values used in the present technology. Alternatively, an automatic sensitivity control circuit may be used to effectively deal with signals of varying amplitude.

The outputs of the atrial and ventricular sensing circuits, 782 and 784, are connected to the microcontroller 760 which, in turn, are able to trigger or inhibit the atrial and ventricular pulse generators, 770 and 772, respectively, in a demand fashion in response to the absence or presence of cardiac activity, in the appropriate chambers of the heart. The sensing circuits, 782 and 784, in turn, receive control signals over signal lines, 786 and 788, from the microcontroller 760 for purposes of measuring cardiac performance at appropriate times, and for controlling the gain, threshold, polarization charge removal circuitry (not shown), and timing of any blocking circuitry (not shown) coupled to the inputs of the sensing circuits, 782 and 786.

For arrhythmia detection, the device 610 includes an arrhythmia detector 762 that utilizes the atrial and ventricular sensing circuits, 782 and 784, to sense cardiac signals to determine whether a rhythm is physiologic or pathologic. The timing intervals between sensed events (e.g., P-waves, R-waves, and depolarization signals associated with fibrillation) can be classified by the microcontroller 760 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 762 can perform arrhythmia discrimination, e.g., using measures of arterial blood pressure determined in accordance with embodiments of the present technology. The arrhythmia detector 762 can be implemented within the microcontroller 760, as shown in FIG. 7. Thus, this detector 762 can be implemented by software, firmware, or combinations thereof. It is also possible that all, or one or more portion(s), of the arrhythmia detector 762 can be implemented using hardware. Further, it is also possible that all, or one or more portion(s), of the arrhythmia detector 762 can be implemented separate from the microcontroller 760.

In accordance with an embodiment of the present technology, the implantable device 610 includes an arterial blood pressure monitor 769. The arterial blood pressure monitor 769 can be used to monitor the patient's arterial blood pressure and changes therein. Such techniques can include, e.g., detecting one or more predetermined feature(s) of an EGM signal indicative of cardiac electrical activity, detecting one or more predetermined feature(s) of a plethysmography signal indicative of changes in arterial blood volume, and determining time(s) between the predetermined feature(s) of the EGM and the predetermined feature(s) of the plethysmography signal. Such techniques also include estimating arterial blood pressure and changes therein based on such time(s). The arterial blood pressure monitor 769 can also be configured to monitor changes in the patient's arterial blood pressure over a day and/or other lengths of time. Additionally, the arterial blood pressure monitor can cause the storing, within the implantable system (e.g., in memory 794), of information indicative of the monitored arterial blood pressure and changes therein so that the stored information is available for transfer to a non-implanted system. Additionally, based on the estimates of the patient's arterial blood pressure and changes therein, the monitor 769 can trigger an alert, therapy and/or adjust therapy, including but not limited to pacing therapy.

The arterial blood pressure monitor 769 can be implemented within the microcontroller 760, as shown in FIG. 7, and can be implemented by software, firmware, or combinations thereof. It is also possible that all, or one or more portion(s) of arterial blood pressure monitor 769 can be implemented separate from microcontroller 760.

The implantable device 610 can also include a pacing controller 766, which can adjust a pacing rate, pacing intervals and/or pacing configuration based on estimates of arterial blood pressure and/or changes therein, in accordance with embodiments of the present technology. The pacing controller 766 can be implemented within the microcontroller 760, as shown in FIG. 7. Thus, the pacing controller 766 can be implemented by software, firmware, or combinations thereof. It is also possible that all, or one or more portion(s), of the pacing controller 766 can be implemented using hardware. Further, it is also possible that all, or one or more portion(s), of the pacing controller 766 can be implemented separate from the microcontroller 760.

The implantable device can also include a medication pump 703, which can deliver medication to a patient if the patient's arterial blood pressure falls above, below, or outside certain thresholds or ranges. Information regarding exemplary implantable medication pumps may be found in U.S. Pat. No. 4,731,051 (Fischell) and in U.S. Pat. No. 4,947,845 (Davis), both of which are incorporated by reference herein.

Still referring to FIG. 7, cardiac signals are also applied to the inputs of an analog-to-digital (A/D) data acquisition system 790. The data acquisition system 790 can be configured to acquire various signal, including but not limited to, EGM, PPG and IPG signals, convert the raw analog data into a digital signal, and store the digital signals for later processing and/or telemetric transmission to an external device 702. The data acquisition system 790 can be coupled to the right atrial lead 620, the coronary sinus lead 624, and the right ventricular lead 630 through the switch 774 to sample cardiac signals across any pair of desired electrodes.

The data acquisition system 790 can be coupled to the microcontroller 760, or other detection circuitry, for detecting an evoked response from the heart 612 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 760 detects a depolarization signal during a window following a stimulation pulse, the presence of which indicates that capture has occurred. The microcontroller 760 enables capture detection by triggering the ventricular pulse generator 772 to generate a stimulation pulse, starting a capture detection window using the timing control circuitry 779 within the microcontroller 760, and enabling the data acquisition system 790 via control signal 792 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969, 467 (Callaghan et. al.); and U.S. Pat. No. 5,350,410 (Mann et. al.), which patents are hereby incorporated herein by reference. The type of capture detection system used is not critical to the present technology.

The microcontroller 760 is further coupled to the memory 794 by a suitable data/address bus 796, wherein the programmable operating parameters used by the microcontroller 760 are stored and modified, as required, in order to customize the operation of the implantable device 610 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 612 within each respective tier of therapy. The memory 794 can also store data including information about the patient's arterial blood pressure, cardiovascular risk and/or disease progression. The memory 794 can also be used to store physiologic signal segments, such as EGM signal segments, PPG signal segments, IPG signal segments, heart sounds signal segments, but not limited thereto.

The operating parameters of the implantable device 610 may be non-invasively programmed into the memory 794 through a telemetry circuit 701 in telemetric communication with an external device 702, such as a programmer, transtelephonic transceiver, or a diagnostic system analyzer. The telemetry circuit 701 can be activated by the microcontroller 760 by a control signal 706. The telemetry circuit 701 advantageously allows EGM and status information relating to the operation of the device 610 (as contained in the microcontroller 760 or memory 794) to be sent to the external device 702 through an established communication link 704. The telemetry circuit can also be used to transmit one or more physiologic signal segments to the external device 702.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 610 additionally includes a battery 711 which provides operating power to all of the circuits shown in FIG. 7. If the implantable device 610 also employs shocking therapy, the battery 711 should be capable of operating at low current drains for long periods of time, and then be capable of providing high-current pulses (for capacitor charging) when the patient requires a shock pulse. The battery 711 should also have a predictable discharge characteristic so that elective replacement time can be detected.

The implantable device 610 is also shown as including an activity and/or posture sensor 715. Such a sensor 715 can be a simple one dimensional sensor that converts mechanical motion into a detectable electrical signal, such as a back electromagnetic field (BEMF) current or voltage, without requiring any external excitation. Alternatively, the sensor 715 can measure multi-dimensional activity information, such as two or more of acceleration, direction, posture and/or tilt. Examples of multi-dimensional activity sensors include, but are not limited to: the three dimensional accelerometer-based position sensor disclosed in U.S. Pat. No. 6,658,292 to Kroll et al., which is incorporated herein by reference; the AC/DC multi-axis accelerometer disclosed in U.S. Pat. No. 6,466,821 to Pianca et al., which in incorporated herein by reference; and the commercially available precision dual-axis accelerometer model ADXL203 and three-axis accelerometer model ADXL346, both available from Analog Devices of Norwood, Massachusetts.

The implantable device 610 can also include a magnet detection circuitry (not shown), coupled to the microcontroller 760. It is the purpose of the magnet detection circuitry to detect when a magnet is placed over the implantable device 610, which magnet may be used by a clinician to perform various test functions of the implantable device 610 and/or to signal the microcontroller 760 that the external programmer 702 is in place to receive or transmit data to the microcontroller 760 through the telemetry circuits 701.

As further shown in FIG. 7, the device 610 is also shown as having an impedance measuring and processing circuit 713 which is enabled by the microcontroller 760 via a control signal 714 and can be used for obtaining many types of bodily and intracardiac impedances, including a network of single- or multi-vector impedance measurements. Such impedance measurements can be used, e.g., for trending many kinds of physiologic variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring and processing circuit 713 can also be used to produce an IPG signal, of which one or more segments can be stored in the memory 794. The impedance measuring and processing circuit 713 may be coupled to the switch 774 so that any desired electrodes may be used, and networks of vectors can be selected.

In the case where the implantable device 610 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 760 further controls a shocking circuit 716 by way of a control signal 718. The shocking circuit 716 generates shocking pulses of low (up to 0.5 Joules), moderate (0.5-10 Joules), or high energy (11 to 40 Joules), as controlled by the microcontroller 760. Such shocking pulses are applied to the patient's heart 612 through at least two shocking electrodes, and as shown in this embodiment, selected from the left atrial coil electrode 628, the RV coil electrode 636, and/or the SVC coil electrode 638. As noted above, the housing 640 may act as an active electrode in combination with the RV electrode 636, or as part of a split electrical vector using the SVC coil electrode 638 or the left atrial coil electrode 628 (i.e., using the RV electrode as a common electrode).

The above described implantable device 610 was described as an exemplary pacing device that is capable of sensing and storing one or more physiologic signal segments. One or ordinary skill in the art would understand that other types of implantable devices can be used to sense and store one or more physiologic signal segments. For example, the implantable device can be a leadless cardiac pacemaker including at least two electrodes that can be used to sense and store EGM signal segments. For another example, it is possible that physiologic signal segments are sensed and stored by an IMD that does not provide any type of therapy, but rather, is only capable of performing monitoring. An example of such an IMD is an insertable cardiac monitor (ICM).

It is also possible that a non-implanted device, such as a wrist worn device or a chest worn device, or the like, be used to sense and store physiologic signal segments, such as ECG signal segments, or PPG signal segments, but not limited thereto. ECG signal segments may alternatively be sensed using leads that are attached to a patient's body via surface electrodes. It is also possible that ECG signal segments are sensed and stored using a personal ECG monitor that is wirelessly coupled to a smartphone. An example of such a personal ECG monitor is the KARDIAMOBILE™ device available from AliveCor, headquartered in Mountain View, California. Examples of wrist worn devices that are capable of obtaining and storing ECG signal segments include the Apple Watch™ available from Apple Inc., headquartered in Cupertino, California, and wearable devices available from Fitbit, headquartered in San Francisco, California, just to name a few. These types of wearable devices may also be able to obtain other types of physiologic signal segments, such as PPG signal segments. PPG signal segments can also be sensed by other types of non-implantable devices, such as, but not limited to, finger pulse oximeters, which are commonly available in hospitals and other medical facilities.

Example System

Figure 8:
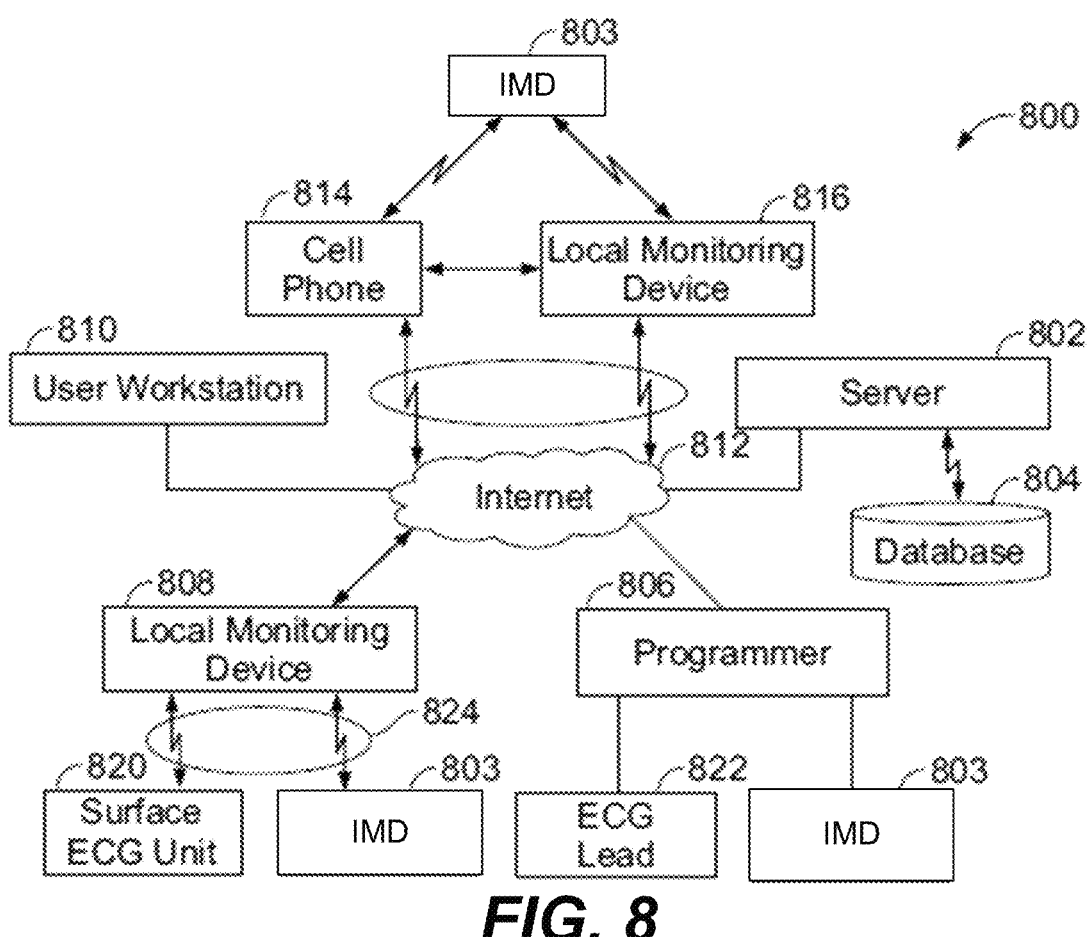
FIG. 8 illustrates an example system that can be used to display one of more of physiologic signal segments, or one or more portion(s) thereof, in accordance with certain embodiments of the present technology.

FIG. 8 illustrates an example system that can be used to display one of more of physiologic signal segments, or one or more portion(s) thereof, in accordance with embodiments of the present technology. In FIG. 8, the system is a distributed processing system 800 that includes a server 802 connected to a database 804, a programmer 806, a local monitoring device 808 (e.g., IMD 100) and a user workstation 810 electrically connected to a network 812. Any one or more of the processor-based components, e.g., workstation 810, cell phone 814, local monitoring device 816, server 802, or programmer 806, but not limited thereto, may perform the processes discussed herein.

The network 812 may provide cloud-based services over the internet, a voice over IP (VoIP) gateway, a local plain old telephone service (POTS), a public switched telephone network (PSTN), a cellular phone-based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 802 is a computer system that includes one or more processors and provides services to the other computing devices on the network 812. The server 802 controls the communication of information, such as physiologic signal segments, bradycardia episode information, asystole episode information, arrythmia episode information, markers, heart rates, and device settings. The server 802 interfaces with the network 812 to transfer information between the programmer 806, local monitoring devices 808, 816, user workstation 810, cell phone 814 and database 804. The database 804 stores information, such as physiologic signal segments, arrythmia episode information, arrythmia statistics, diagnostics, heart rates, device settings, and the like, for a patient population, as well as separated for individual patients, individual physicians, individual clinics, individual medical networks and the like. The programmer 806 may reside in a patient's home, a hospital, or a physician's office. The programmer 806 may wirelessly communicate with the IMD 803 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 806 to the IMD 803. The programmer 806 is, e.g., able to acquire ECG signal segments from surface electrodes on a person, EGM signal segments from the IMD 803, and/or arrythmia episode information, arrythmia statistics, diagnostics, markers, atrial heart rates, device settings from the IMD 803. The programmer 806 interfaces with the network 812, either via the internet, to upload the information acquired from the surface ECG unit 820, or the IMD 803 to the server 802. The IMD 803 can be, e.g., the IMD 610 described above with reference to FIGS. 6 and 7, but is not limited thereto.

The local monitoring device 808 interfaces with the communication system to upload to the server 802 one or more physiologic signal segments, motion data, arrythmia episode information, arrythmia statistics, diagnostics, markers, heart rates, sensitivity profile parameter settings and detection thresholds. In one embodiment, the surface ECG unit 820 and the IMD 803 have a bi-directional connection 824 with the local RF monitoring device 808 via a wireless connection. The local monitoring device 808 is able to acquire surface ECG signal segments from one or more ECG leads 822, as well as other information from the IMD 803. On the other hand, the local monitoring device 808 may download the data and information discussed herein from the database 804 to the IMD 803. It would also be possible for pulse oximeter sensor that obtains PPG segments to be communicatively coupled to one of the local monitoring devices 808, 816, or the programmer 806, or a cell phone 814.

The user workstation 810, cell phone 814 and/or programmer 806 may be utilized by a physician or medical personnel to interface with the network 812 to download physiologic signal segments, motion data, and other information discussed herein from the database 804, from the local monitoring devices 808, 816, from the IMD 803 or otherwise. Once downloaded, the user workstation 810 may process the physiologic signal segments and cause the display of portions thereof in accordance with one or more of the operations described above. The user workstation 810, cell phone 814 and/or programmer 806, may be used to display portions of physiologic signal segments to a clinician, in accordance with embodiments of the present technology described herein.

The user workstation 810, cell phone 814 and/or programmer 806 may upload/push settings, IMD instructions, other information and notifications to the cell phone 814, local monitoring devices 808, 816, programmer 806, server 802 and/or IMD 803. The user workstation 810, cell phone 814 and/or programmer 806 can each include, or be communicatively coupled to, a display screen, so that portions of physiologic signal segments can be displayed on the display screen utilizing embodiments of the present technology. The user workstation 810, cell phone 814 and/or programmer 806 can each include, or be communicatively coupled to, a printer so that portions of physiologic signal segments can be displayed on a printout (aka a printed report) utilizing embodiments of the present technology.

Figure 9:
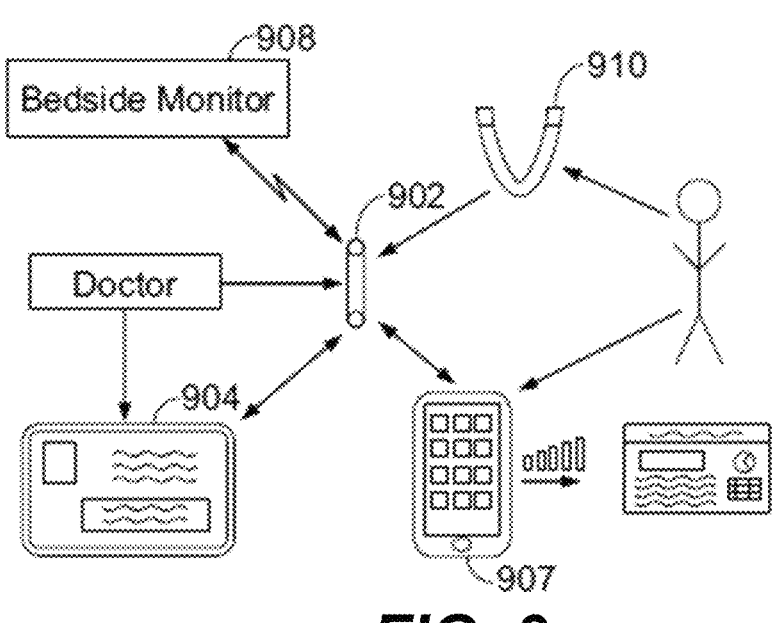
FIG. 9 illustrates a system level diagram indicating potential devices and networks that utilize the methods and systems herein.

The system of FIG. 8 further comprises one or more processors configured to execute the specific executable instructions to perform the steps described above with reference to FIG. 2. FIG. 9 illustrates a system level diagram indicating potential devices and networks that utilize the methods and systems herein. For example, an IMD 902 may be utilized to sense and store physical signal segments. The IMD 902 may supply the physiologic signal segments to various local external devices, such as a tablet device 904, a smart phone 906, a bedside monitoring device 908, a smart watch and the like. The devices 904-908 can include, or be communicatively coupled to, a display screen to enable physiologic signal segments, or one or more portion(s) thereof, to be displayed a clinician or the like. The devices can also include, or communicatively coupled to, a printer that can print physiologic signal segments, or one or more portion(s) thereof, for display and analysis by a clinician or the like.

The IMD 902 may convey the physiologic signal segments over various types of wireless communications links to the devices 904, 906 and 908. The IMD 902 may utilize various communications protocols and be activated in various manners, such as through a Bluetooth, Bluetooth low energy, Wi-Fi or other wireless protocol. Additionally or alternatively, when a magnetic device 910 is held next to the patient, the magnetic field from the device 910 may activate the IMD 902 to transmit the physiologic signal segments and other information, such as arrythmia data, to one or more of the devices 904-908.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for improving visibility of features of a physiologic signal segment that is to be displayed within a display band having a specified height between an upper boundary and a lower boundary of the display band, the method comprising:

obtaining the physiologic signal segment, which is indicative of physiologic activity of a patient for a period of time that includes a plurality of cycles of the physiologic activity, wherein the physiologic signal segment has an original signal segment range that extends from an original minimum peak amplitude of the physiologic signal segment to an original maximum peak amplitude of the physiologic signal segment;

dividing the physiologic signal segment into a plurality of sub-segments;

determining a sub-segment minimum peak amplitude and a sub-segment maximum peak amplitude, for each of the plurality of sub-segments, to thereby determine a plurality of sub-segment minimum peak amplitudes and a plurality of sub-segment maximum peak amplitudes;

determining a new minimum peak amplitude based on the plurality of sub-segment minimum peak amplitudes, and a new maximum peak amplitude based on the plurality of sub-segment maximum peak amplitudes;

determining a new display range as being from the new minimum peak amplitude to the new maximum peak amplitude, wherein the new display range is narrower than the original signal segment range; and causing displaying, within the display band having the specified height, of a portion of the physiologic signal segment that is within the new display range, such that the upper boundary of the display band corresponds to the new maximum peak amplitude, and the lower boundary of the display band corresponds to the new minimum peak amplitude.

2. The method of claim 1, further comprising:

determining a new gain level based on the new display range and the specified height of the display band; and causing further displaying, within or proximate to the display band, of at least one of the new gain level, a scale indicator determined based on the new gain level, or a surrogate of the scale indicator, to thereby enable someone viewing the display band to discern magnitudes of the features of the portion of the physiologic signal segment being displayed within the display band.

3. The method of claim 2, further comprising:
determining the scale indicator by determining a quotient of the specified height of the display band divided by the new gain level; and
wherein the causing further displaying comprises causing displaying of the scale indicator or the surrogate of the scale indicator in at least one of the following manners:
cause displaying of one or more values along a vertical axis of the display band based on the scale indicator; or
cause displaying of the scale indicator next to a vertical line or square wave within or proximate to the display band.

4. The method of claim 2, wherein:
the determining the new gain level comprises determining a quotient of the specified height of the display band divided by the new display range.

5. The method of claim 1, wherein:
the causing displaying, within the display band having the specified height, of portions of the physiologic signal segment that are within the new display range, such that the upper boundary of the display band corresponds to the new maximum peak amplitude, and the lower boundary of the display band corresponds to the new minimum peak amplitude, magnifies features of the physiologic signal segment that are within the new display range, compared to if an entirety of the physiologic signal segment within the original signal segment range were instead caused to be displayed within the display band having the specified height such that the upper boundary of the display band corresponded to the original maximum peak amplitude of the physiologic signal segment, and the lower boundary of the display band corresponded to the original minimum peak amplitude of the physiologic signal segment.

6. The method of claim 1, further comprising:
after the obtaining the physiologic signal segment, and prior to performing any other steps of claim 1:
determining a threshold signal range by determining a quotient of the specified height of the display band divided by an original gain level; and
determining whether the original signal segment range exceeds the threshold signal range; and
performing the other steps of claim 1, in response to the original signal segment range exceeding the threshold signal range.

7. The method of claim 1, wherein:
the determining the new minimum peak amplitude, based on the plurality of sub-segment minimum peak amplitudes, comprises:
determining a first outlier threshold based on the plurality of sub-segment minimum peak amplitudes;
separating the plurality of sub-segment minimum peak amplitudes into first and second subsets thereof, such that the first subset includes each of the sub-segment minimum peak amplitudes that is less than the first outlier threshold, and the second subset includes each of the sub-segment minimum peak amplitudes that is not less than the first outlier threshold;
determining a first candidate for being the new minimum peak amplitude based on the first subset of the plurality of sub-segment minimum peak amplitudes, and a second candidate for being the new minimum peak amplitude based on the second subset of the plurality of sub-segment minimum peak amplitudes; and selecting, as the new minimum peak amplitude, a minimum one of the first and second candidates for being the new minimum peak amplitude; and
the determining the new maximum peak amplitude, based on the plurality of sub-segment maximum peak amplitudes, comprises:
determining a second outlier threshold based on the plurality of sub-segment maximum peak amplitudes;
separating the plurality of sub-segment maximum peak amplitudes into first and second subsets thereof, such that the first subset includes each of the sub-segment maximum peak amplitudes that are that is greater than the second outlier threshold, and the second subset includes each of the sub-segment maximum peak amplitudes that is not greater than the second outlier threshold;
determining a first candidate for being the new maximum peak amplitude based on the first subset of the plurality of sub-segment maximum peak amplitudes, and a second candidate for being the new maximum peak amplitude based on the second subset of the plurality of sub-segment maximum peak amplitudes; and
selecting, as the new maximum peak amplitude, a maximum one of the first and second candidates for being the new maximum peak amplitude.

8. The method of claim 7, wherein:
the determining the first outlier threshold based on the plurality of sub-segment minimum peak amplitudes comprises:
determining a 25% quartile value and an inter-quartile range (IQR) of the plurality of sub-segment minimum peak amplitudes; and
determining the first outlier threshold based on the 25% quartile value and the IQR of the plurality of sub-segment minimum peak amplitudes; and
the determining the second outlier threshold based on the plurality of sub-segment maximum peak amplitudes comprises:
determining a 75% quartile value and an inter-quartile range (IQR) of the plurality of sub-segment maximum peak amplitudes; and
determining the second outlier threshold based on the 75% quartile value and the IQR of the plurality of sub-segment maximum peak amplitudes.

9. The method of claim 7, wherein:
the determining the first outlier threshold based on the plurality of sub-segment minimum peak amplitudes comprises:
determining a mean and a standard deviation (SD) of the plurality of sub-segment minimum peak amplitudes; and
determining the first outlier threshold based on the mean and the SD of the plurality of sub-segment minimum peak amplitudes; and
the determining the second outlier threshold based on the plurality of sub-segment maximum peak amplitudes comprises:
determining a mean and a standard deviation (SD) of the plurality of sub-segment maximum peak amplitudes; and
determining the second outlier threshold based on the mean and the SD of the plurality of sub-segment maximum peak amplitudes.

10. The method of claim 1, wherein the physiologic signal segment is indicative of one of the following:

33 cardiac electrical activity of the patient for a period of
time that includes a plurality of cardiac cycles;
cardiac mechanical activity of the patient for a period of
time that includes a plurality of cardiac cycles; or
respiratory activity of the patient for a period of time that
includes a plurality of respiratory cycles.

11. The method of claim 1, wherein:
the determining the new minimum peak amplitude com-
prises determining first and second candidates for being
the new minimum peak amplitude, based on the plu-
rality of sub-segment minimum peak amplitudes, and
selecting as the new minimum peak amplitude a mini-
mum one of the first and second candidates for being
the new minimum peak amplitude; and
the determining the new maximum peak amplitude com-
prises determining first and second candidates for being
the new maximum peak amplitude, based on the plu-
rality of sub-segment maximum peak amplitudes, and
selecting as the new maximum peak amplitude a maxi-
mum one of the first and second candidates for being
the new maximum peak amplitude.

12. The method of claim 1, further comprising:
causing displaying, below the display band, of a marker
band that includes one or more marker symbols corre-
sponding to one or more physiologic events represented
in the physiologic signal segment displayed within the
display band; and
wherein a lower portion of the physiologic signal segment
that is displayed extends beyond the lower boundary of
the display band, such the lower portion of the physi-
ologic signal segment extends into and overlaps the
marker band.

13. A system for improving visibility of features of a
physiologic signal segment that is to be displayed within a
display band having a specified height between an upper
boundary and a lower boundary of the display band, the
system comprising:
memory configured to store specific executable instruc-
tions; and
one or more processors configured to execute the specific
executable instructions to:
obtain the physiologic signal segment, which is indica-
tive of physiologic activity of a patient for a period
of time that includes a plurality of cycles of the
physiologic activity, wherein the physiologic signal
segment has an original signal segment range that
extends from an original minimum peak amplitude
of the physiologic signal segment to an original
maximum peak amplitude of the physiologic signal
segment;
divide the physiologic signal segment into a plurality of
sub-segments;
determine a sub-segment minimum peak amplitude and
a sub-segment maximum peak amplitude, for each of
the plurality of sub-segments, to thereby determine a
plurality of sub-segment minimum peak amplitudes
and a plurality of sub-segment maximum peak
amplitudes;
determine a new minimum peak amplitude based on the
plurality of sub-segment minimum peak amplitudes,
and a new maximum peak amplitude based on the
plurality of sub-segment maximum peak amplitudes;
determine a new display range as being from the new
minimum peak amplitude to the new maximum peak
amplitude, wherein the new display range is nar-
rower than the original signal segment range; and

34 cause display, within the display band having the
specified height, of a portion of the physiologic
signal segment that is within the new display range,
such that the upper boundary of the display band
corresponds to the new maximum peak amplitude,
and the lower boundary of the display band corre-
sponds to the new minimum peak amplitude.

14. The system of claim 13, wherein the one or more
processors are further configured to:
determine a new gain level based on the new display
range and the specified height of the display band; and
cause further display, within or proximate to the display
band, of at least one of the new gain level, a scale
indicator determined based on the new gain level, or a
surrogate of the scale indicator, to thereby enable
someone viewing the display band to discern magni-
tudes of the features of the portion of the physiologic
signal segment being displayed within the display
band.

15. The system of claim 14, wherein the one or more
processors are further configured to:
determine the scale indicator by determining a quotient of
the specified height of the display band divided by the
new gain level; and
wherein the scale indicator or the surrogate of the scale
indicator is caused to be displayed in at least one of the
following manners:
cause display of one or more values along a vertical
axis of the display band based on the scale indicator;
or
cause display of the scale indicator next to a vertical
line or square wave within or proximate to the
display band.

16. The system of claim 14, wherein the one or more
processors are further configured to determine the new gain
level by determining a quotient of the specified height of the
display band divided by the new display range.

17. The system of claim 13, wherein:
the cause display, within the display band having the
specified height, of portions of the physiologic signal
segment that are within the new display range, such that
the upper boundary of the display band corresponds to
the new maximum peak amplitude, and the lower
boundary of the display band corresponds to the new
minimum peak amplitude, magnifies features of the
physiologic signal segment that are within the new
display range, compared to if an entirety of the physi-
ologic signal segment within the original signal seg-
ment range were instead caused to be displayed within
the display band having the specified height such that
the upper boundary of the display band corresponded to
the original maximum peak amplitude of the physi-
ologic signal segment, and the lower boundary of the
display band corresponded to the original minimum
peak amplitude of the physiologic signal segment.

18. The system of claim 13, wherein, after the physiologic
signal segment is obtained, the specific executable instruc-
tions are configured to:
determine a threshold signal range by determining a
quotient of the specified height of the display band
divided by an original gain level; and
determine whether the original signal segment range
exceeds the threshold signal range; and
cause display, within the display band having the specified
height, of the portion of the physiologic signal segment that is within the new display range, when the original signal segment range exceeding the threshold signal range.

19. The system of claim 13, wherein the one or more processors are further configured to:

determine the new minimum peak amplitude, based on the plurality of sub-segment minimum peak amplitudes, by:

determining a first outlier threshold based on the plurality of sub-segment minimum peak amplitudes;

separating the plurality of sub-segment minimum peak amplitudes into first and second subsets thereof, such that the first subset includes each of the sub-segment minimum peak amplitudes that is less than the first outlier threshold, and the second subset includes each of the sub-segment minimum peak amplitudes that is not less than the first outlier threshold;

determining a first candidate for being the new minimum peak amplitude based on the first subset of the plurality of sub-segment minimum peak amplitudes, and a second candidate for being the new minimum peak amplitude based on the second subset of the plurality of sub-segment minimum peak amplitudes; and selecting, as the new minimum peak amplitude, a minimum one of the first and second candidates for being the new minimum peak amplitude; and determine the new maximum peak amplitude, based on the plurality of sub-segment maximum peak amplitudes, by:

determining a second outlier threshold based on the plurality of sub-segment maximum peak amplitudes;

separating the plurality of sub-segment maximum peak amplitudes into first and second subsets thereof, such that the first subset includes each of the sub-segment maximum peak amplitudes that is greater than the second outlier threshold, and the second subset includes each of the sub-segment maximum peak amplitudes that is not greater than the second outlier threshold;

determining a first candidate for being the new maximum peak amplitude based on the first subset of the plurality of sub-segment maximum peak amplitudes, and a second candidate for being the new maximum peak amplitude based on the second subset of the plurality of sub-segment maximum peak amplitudes; and selecting, as the new maximum peak amplitude, a maximum one of the first and second candidates for being the new maximum peak amplitude.

20. The system of claim 19, wherein:

the determining the first outlier threshold based on the plurality of sub-segment minimum peak amplitudes comprises:

determining a 25% quartile value and an inter-quartile range (IQR) of the plurality of sub-segment minimum peak amplitudes; and determining the first outlier threshold based on the 25% quartile value and the IQR of the plurality of sub-segment minimum peak amplitudes; and the determining the second outlier threshold based on the plurality of sub-segment maximum peak amplitudes comprises:

determining a 75% quartile value and an inter-quartile range (IQR) of the plurality of sub-segment maximum peak amplitudes; and determining the second outlier threshold based on the 75% quartile value and the IQR of the plurality of sub-segment maximum peak amplitudes.

21. The system of claim 19, wherein:

the determining the first outlier threshold based on the plurality of sub-segment minimum peak amplitudes comprises:

determining a mean and a standard deviation (SD) of the plurality of sub-segment minimum peak amplitudes; and determining the first outlier threshold based on the mean and the SD of the plurality of sub-segment minimum peak amplitudes; and the determining the second outlier threshold based on the plurality of sub-segment maximum peak amplitudes comprises:

determining a mean and a standard deviation (SD) of the plurality of sub-segment maximum peak amplitudes; and determining the second outlier threshold based on the mean and the SD of the plurality of sub-segment maximum peak amplitudes.

22. The system of claim 13, wherein the physiologic signal segment is indicative of one of the following:

cardiac electrical activity of the patient for a period of time that includes a plurality of cardiac cycles;

cardiac mechanical activity of the patient for a period of time that includes a plurality of cardiac cycles; or respiratory activity of the patient for a period of time that includes a plurality of respiratory cycles.

23. The system of claim 13, wherein the one or more processors are further configured to:

determine the new minimum peak amplitude by determining first and second candidates for being the new minimum peak amplitude, based on the plurality of sub-segment minimum peak amplitudes, and selecting as the new minimum peak amplitude a minimum one of the first and second candidates for being the new minimum peak amplitude; and determine the new maximum peak amplitude by determining first and second candidates for being the new maximum peak amplitude, based on the plurality of sub-segment maximum peak amplitudes, and selecting as the new maximum peak amplitude a maximum one of the first and second candidates for being the new maximum peak amplitude.

24. The system of claim 13, wherein the one or more processors are further configured to:

cause displaying, below the display band, of a marker band that includes one or more marker symbols corresponding to one or more physiologic events represented in the physiologic signal segment displayed within the display band; and wherein a lower portion of the physiologic signal segment that is displayed extends beyond the lower boundary of the display band, such the lower portion of the physiologic signal segment extends into and overlaps the marker band.

25. One or more processor readable non-transitory storage devices having instructions encoded thereon which when executed cause one or more processors to perform a method for improving visibility of features of a physiologic signal segment that is to be displayed within a display band having a specified height between an upper boundary and a lower boundary of the display band, the method comprising:

obtaining the physiologic signal segment, which is indicative of physiologic activity of a patient for a period of time that includes a plurality of cycles of the physiologic activity, wherein the physiologic signal segment has an original signal segment range that extends from an original minimum peak amplitude of the physiologic signal segment to an original maximum peak amplitude of the physiologic signal segment;

dividing the physiologic signal segment into a plurality of sub-segments;

determining a sub-segment minimum peak amplitude and a sub-segment maximum peak amplitude, for each of the plurality of sub-segments, to thereby determine a plurality of sub-segment minimum peak amplitudes and a plurality of sub-segment maximum peak amplitudes;

determining a new minimum peak amplitude based on the plurality of sub-segment minimum peak amplitudes, and a new maximum peak amplitude based on the plurality of sub-segment maximum peak amplitudes;

determining a new display range as being from the new minimum peak amplitude to the new maximum peak amplitude, wherein the new display range is narrower than the original signal segment range; and causing displaying, within the display band having the specified height, of a portion of the physiologic signal segment that is within the new display range, such that the upper boundary of the display band corresponds to the new maximum peak amplitude, and the lower boundary of the display band corresponds to the new minimum peak amplitude.

* * * * *